US010195158B2

(12) United States Patent
Gundloori

(10) Patent No.: US 10,195,158 B2
(45) Date of Patent: Feb. 5, 2019

(54) BIOACTIVE OIL BASED POLYESTERAMIDE NANOFIBERS FOR WOUND HEALING APPLICATIONS

(71) Applicant: Council of Scientific and Industrial Research, New Delhi (IN)

(72) Inventor: Rathna Venkata Naga Gundloori, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/116,021

(22) PCT Filed: Apr. 13, 2015

(86) PCT No.: PCT/IN2015/000167
§ 371 (c)(1),
(2) Date: Aug. 2, 2016

(87) PCT Pub. No.: WO2015/159305
PCT Pub. Date: Oct. 22, 2015

(65) Prior Publication Data
US 2017/0135963 A1 May 18, 2017

(30) Foreign Application Priority Data
Apr. 13, 2014 (IN) .......................... 0088/DEL/2014

(51) Int. Cl.
| | | |
|---|---|---|
| *A61K 31/785* | (2006.01) | |
| *D01F 6/94* | (2006.01) | |
| *A61L 15/44* | (2006.01) | |
| *D01D 5/00* | (2006.01) | |
| *A61K 31/43* | (2006.01) | |
| *A61L 15/22* | (2006.01) | |
| *A61K 9/70* | (2006.01) | |
| *A61K 31/155* | (2006.01) | |
| *A61K 31/7036* | (2006.01) | |

(52) U.S. Cl.
CPC .............. *A61K 9/70* (2013.01); *A61K 9/7007* (2013.01); *A61K 31/155* (2013.01); *A61K 31/43* (2013.01); *A61K 31/7036* (2013.01); *A61K 31/785* (2013.01); *A61L 15/225* (2013.01); *A61L 15/44* (2013.01); *D01D 5/003* (2013.01); *D01F 6/94* (2013.01); *A61L 2400/12* (2013.01); *D10B 2509/022* (2013.01)

(58) Field of Classification Search
CPC ......... A61K 9/70; A61K 31/43; A61K 31/785
See application file for complete search history.

(56) References Cited

U.S. PATENT DOCUMENTS

2006/0024357 A1    2/2006  Carpenter et al.
2010/0215939 A1*   8/2010  Westbroek ........... D01D 5/0061
                                                   428/292.1

FOREIGN PATENT DOCUMENTS

| CA | 2161196 C | 1/2005 |
|---|---|---|
| CN | 102824641 A | 12/2012 |
| EP | 2588659 B1 | 3/2016 |
| WO | WO 2009/102451 A1 | 8/2009 |

OTHER PUBLICATIONS

Zafar et al. Reactive & Functional Polymers, Studies on zinc-containing linseed oil based polyesteramide, 2007, 67, 928-935.*
Kim et al. Sci. Technol. Adv. Matter, Temperature-responsive electrospun nanofibers for 'on-off' switchable release of dextran, 2012, 13, 1-9.*
Alam, Manawwer, et al., "Vegetable oil based eco-friendly coating materials: A review article", *Arabian Journal of Chemistry*, Dec. 31, 2013, pp. 469-479, vol. 7, No. 4, Elsevier, BV, Amsterdam.
Chong, E. J., et al, "Evaluation of electrospun PCL/gelatin nanofibrous scaffold for wound healing and layered dernal reconstitution", *Acta Biomaterialia*, Apr. 14, 2007, pp. 321-330, vol. 3, No. 3, Elsevier, BV, Amsterdam.
Gundloori, Rathna Venkata Naga, et al., "Development of non-woven nanofibers of egg albumen-poly (vinyl alcohol) blends: influence of solution properties on morphology of nanofibers", *Polymer Journal*, JUl. 2011, pp. 654-661, vol. 43, No. 7, The Society of Polymer Science, Japan.
International Searching Authority, International Search Report and Written Opinion for International Application No. PCT/IN2015/000167, Aug. 10, 2015, 12 pages, European Patent Office, Netherlands.
Kenawy, El-Refaie, et al., "Release of tetracycline hydrochloride from electrospun poly(ethylene-co-vinylacetate), poly(lactic acid), and a blend", *Journal of Controlled Relsease*, May 2002, pp. 57-64, vol. 81, No. 1-2, Elsevier, BV, Amsterdam.
Pandey, Komal, et al., "Egg albumin based non-woven nanfiber scaffolds for tissue engineering (Abstract)", Proceedings of PolyTech 2012, International Conference on Advances in Polymeric Materials & Nanotechnology, Dec. 15-17, 2012, pp. 159-160, retrieved from <https://independent.academia.edu/> on Jul. 28, 2016.
Pramanik, Sujata, et al., "Bio-degradable vegetable oil based hyperbranced poly(ester amide) as an advanced surface coating material", *Progress In Organic Coatings*, Apr. 2013, pp. 689-697, vol. 76, No. 4, Elsevier, BV, Amsterdam.
Zafar, Fahmina, et al., "Studies on Ambient Cured Biobased Mn(II), Co(II) and Cu(II) Containing Metallopolyesteramides", *Journal of Inorganic and Organometallic Polymers*, Jun. 26, 2011, pp. 646-654, vol. 21, No. 3, Kluwer Academic Publishers-Plenum Publishers, NE.

* cited by examiner

*Primary Examiner* — Sreenivasan Padmanabhan
*Assistant Examiner* — Genevieve S Alley
(74) *Attorney, Agent, or Firm* — Alston & Bird LLP

(57) ABSTRACT

Biocompatible and biodegradable nanofibers are provided. The biocompatible and biodegradable nanofibers include an oil based polyesteramide, a protein/polysaccharide, and a pharmaceutical drug useful for wound healing and biomedical applications thereof.

8 Claims, 17 Drawing Sheets
(7 of 17 Drawing Sheet(s) Filed in Color)

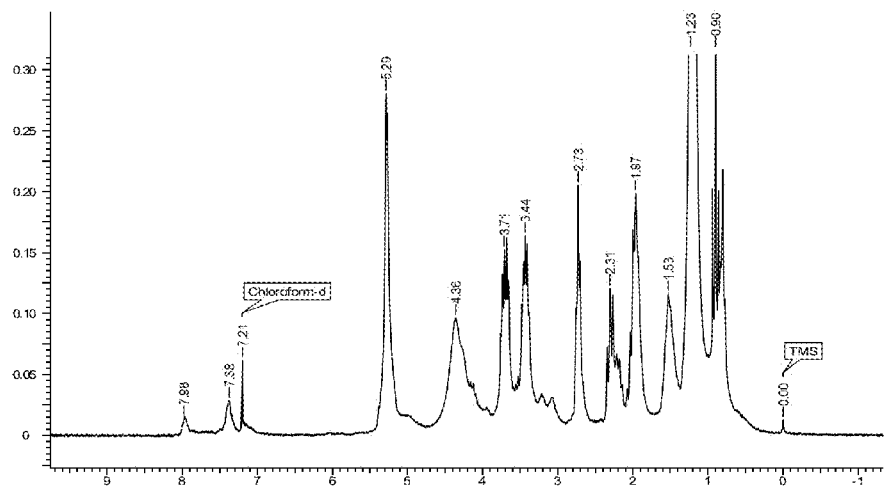
Figure 5
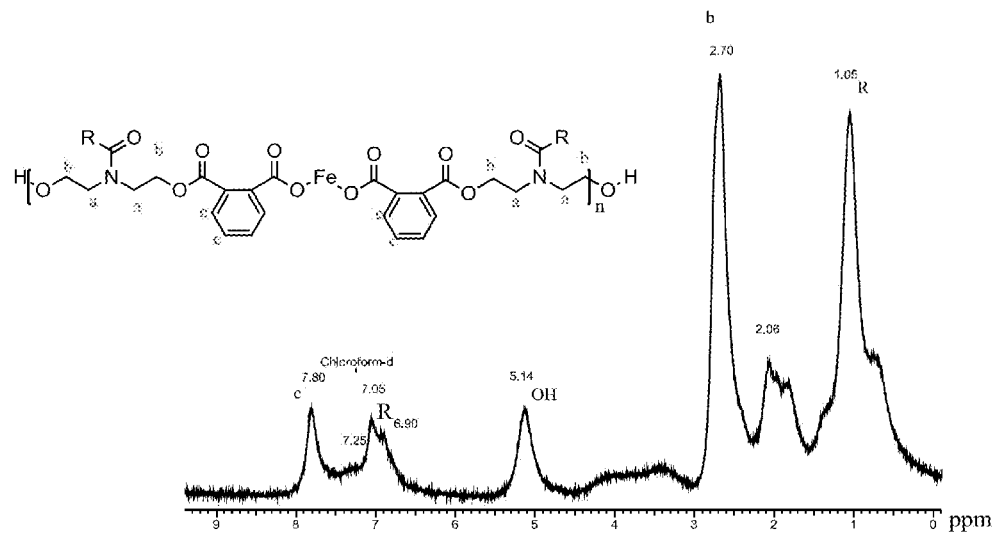
Figure 6 FE-PEA

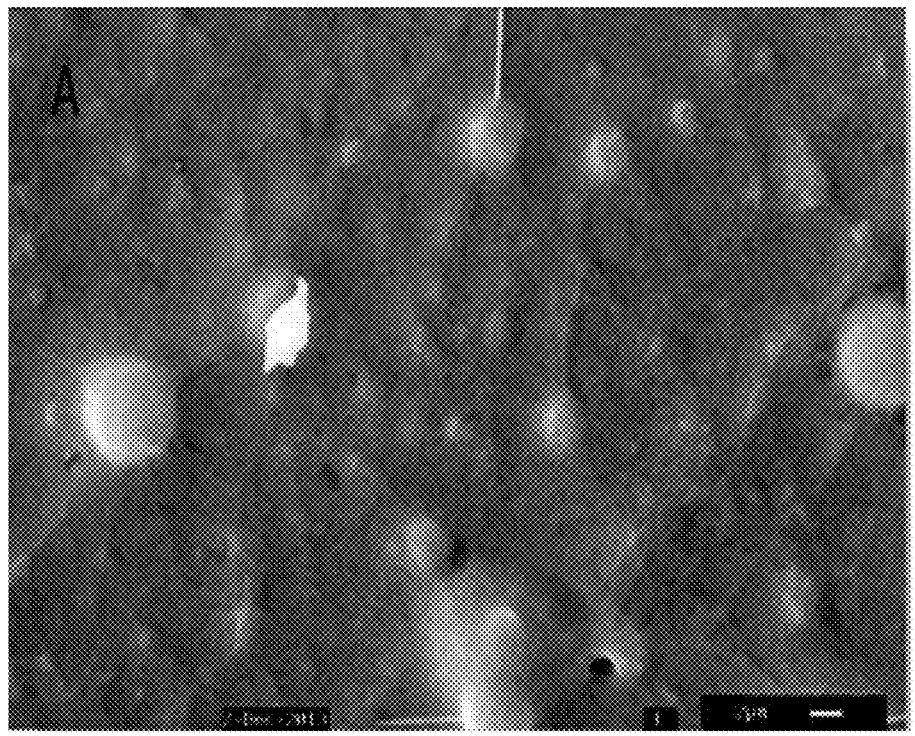
Figure 11: A-SEM images of 1%PHBV+2%EA+7%PEA(S-1),
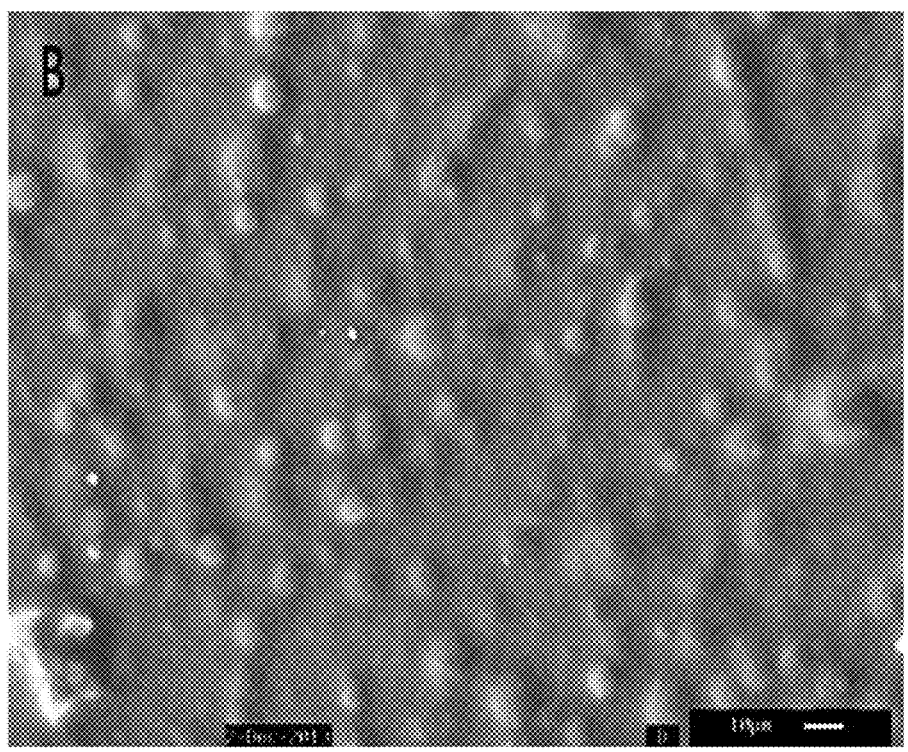
Figure 11: B-SEM image of 2%PHBV+2%EA+7%PEA(S-2),

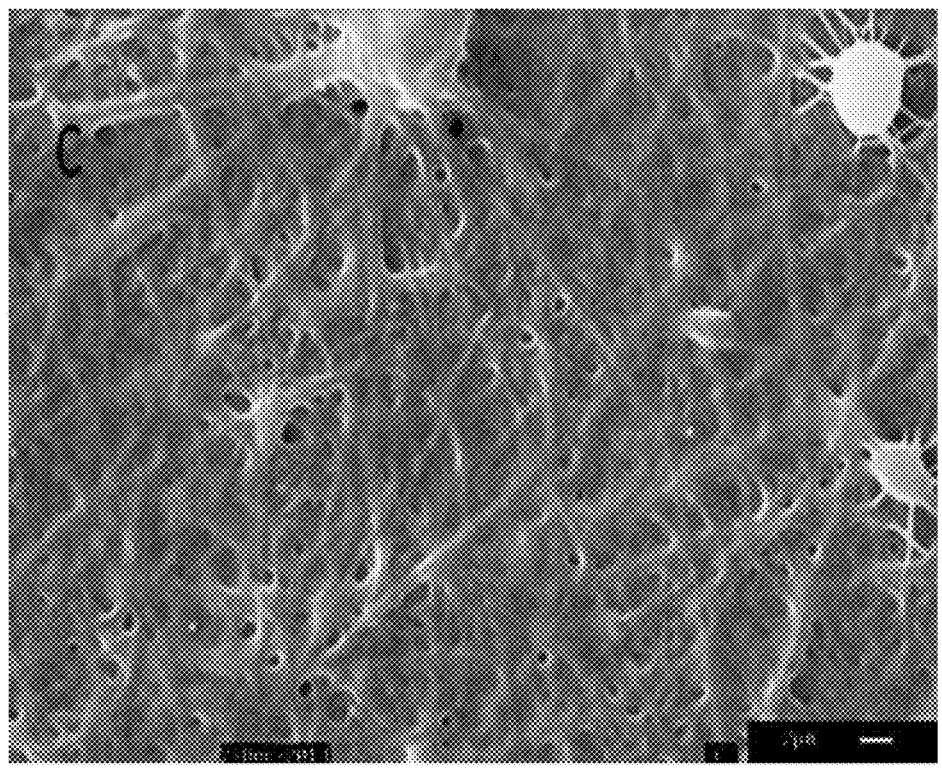
Figure 11: C-SEM image of 3%PHBV+2%EA+5%PEA(S-3),
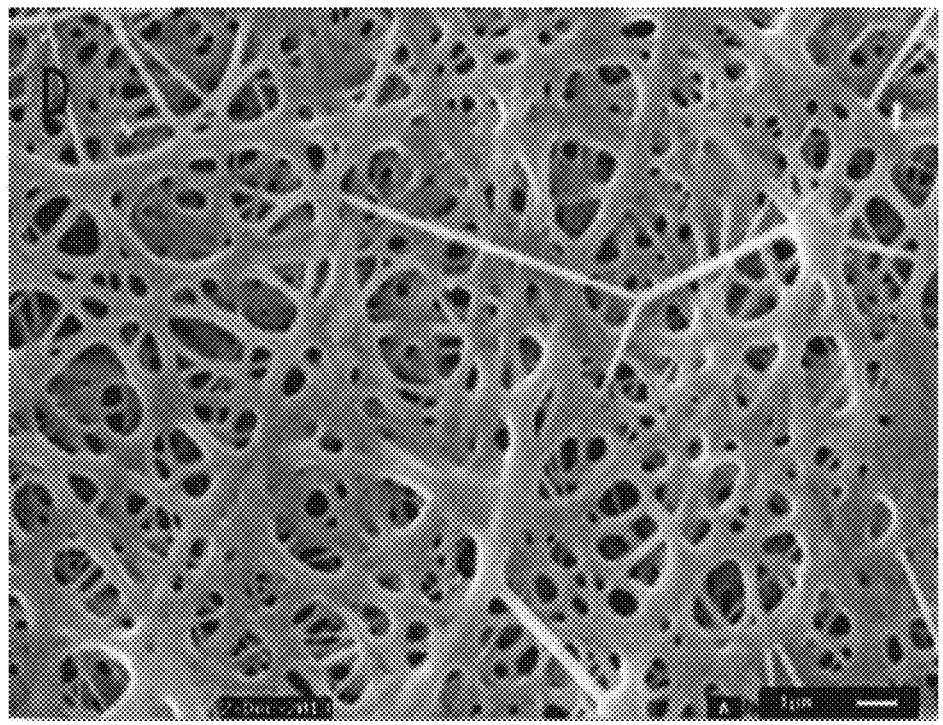
Figure 11: D-SEM image of 4%PHBV+2%EA+6%PEA(S-4),

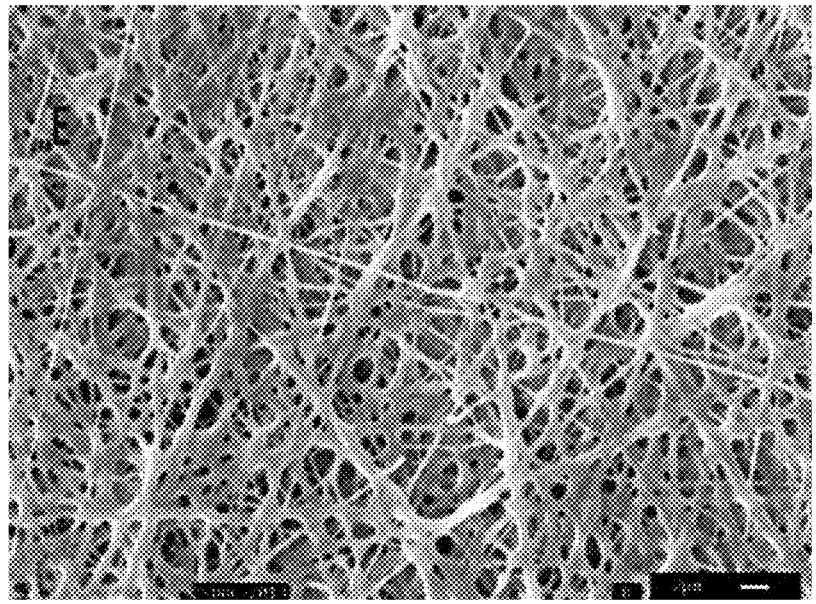
Figure 11: E-SEM image of 5%PHBV+2%EA+3%PEA(S-5)
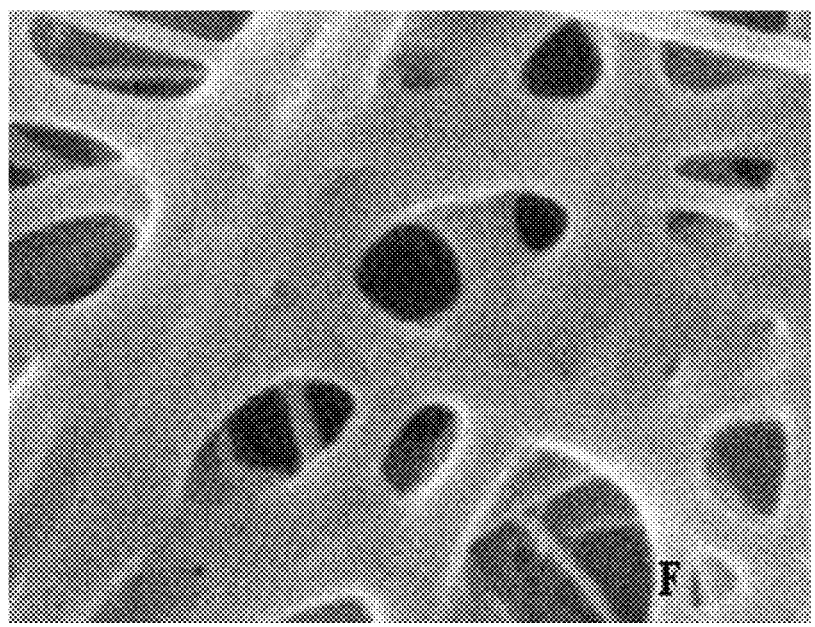
Figure 12: F-Crosslinked SEM image of 5% PHBV+2%EA+3%PEA Without drug (S-5),

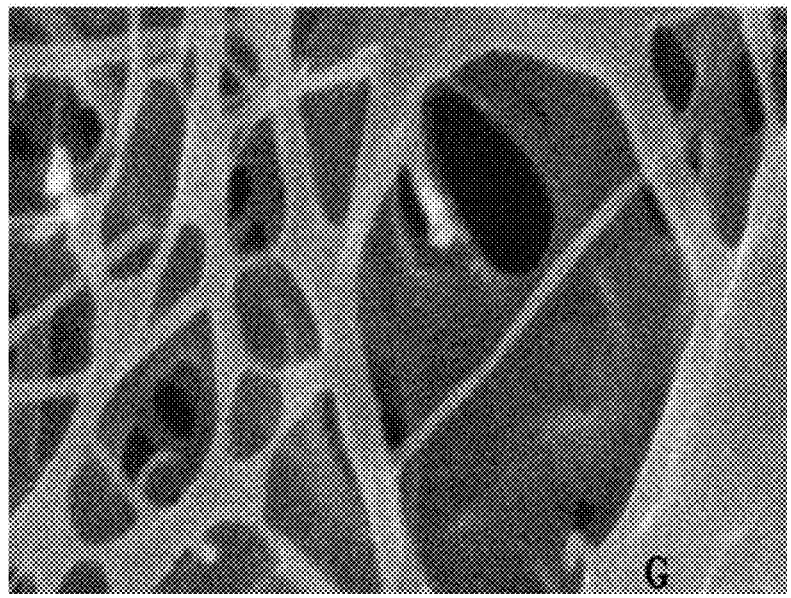
Figure 12: G-Crosslinked SEM image of 5% PHBV+2%EA+3%PEA+10% Drug (S-7),
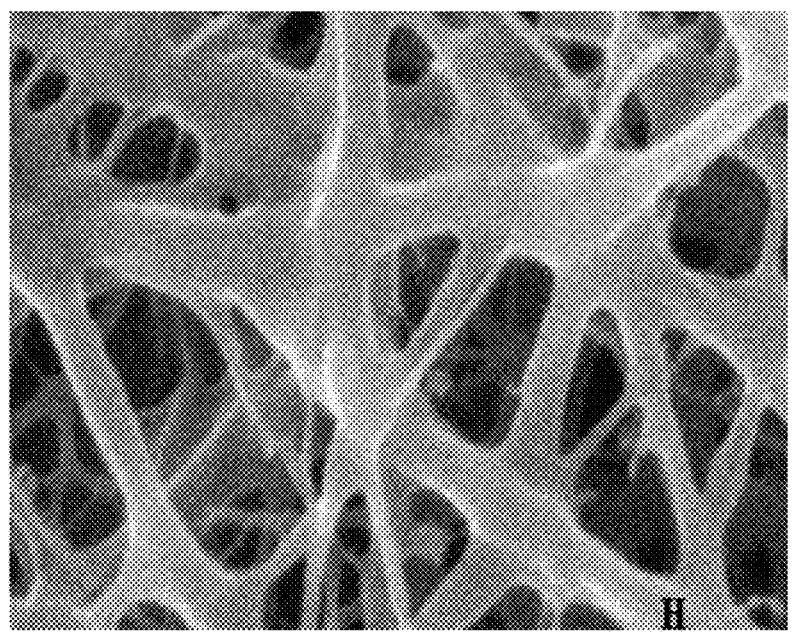
Figure 12: H-Crosslinked SEM image of 5% PHBV+2%EA+3%PEA+15% Drug (S-8),

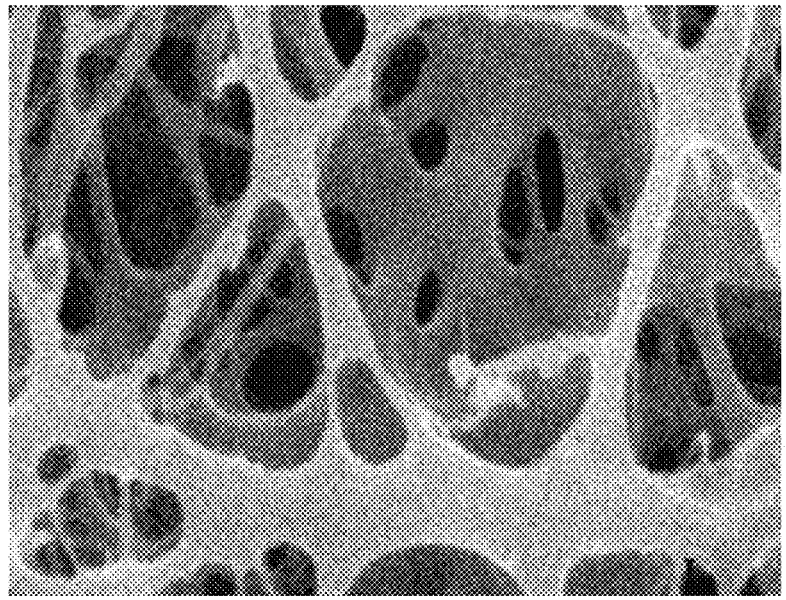
Figure 12: I-Crosslinked SEM image of 5% PHBV+2%EA+3%PEA+20% Drug (S-9).
Figure 13

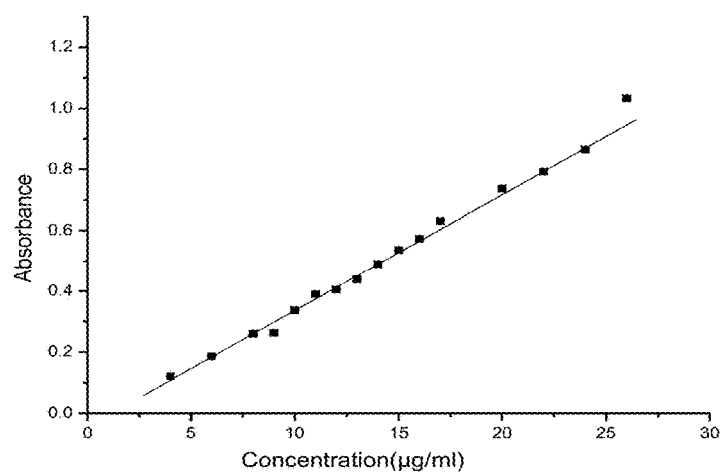
Figure 16
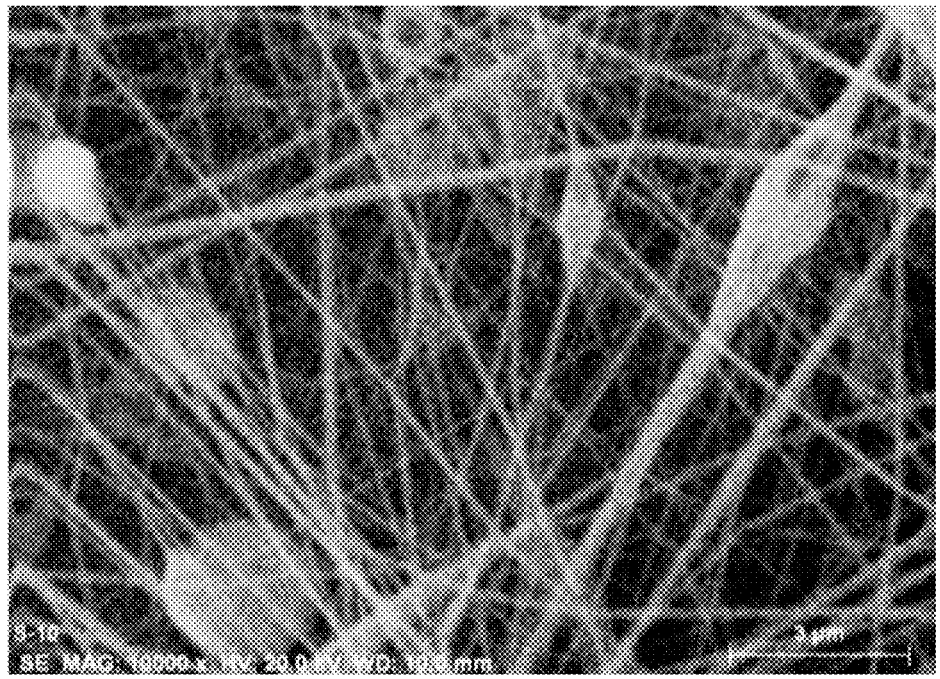
Figure 17(A): 3%PEA, 8%PLA, 2%HSA

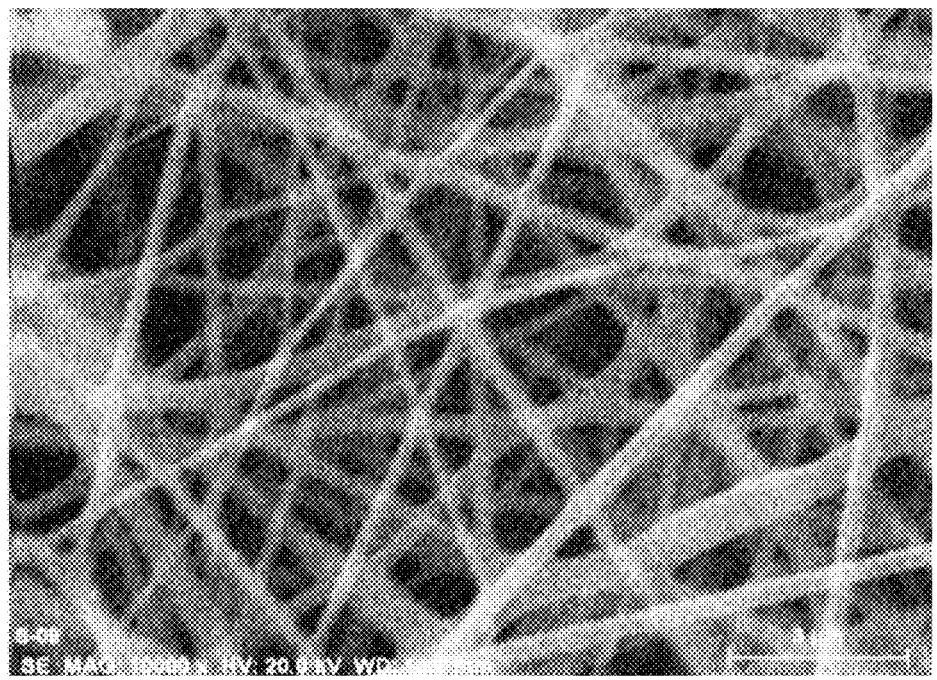
Figure 17(B): 3%PEA, 8%PLA, 2%HSA with 10% triclosan
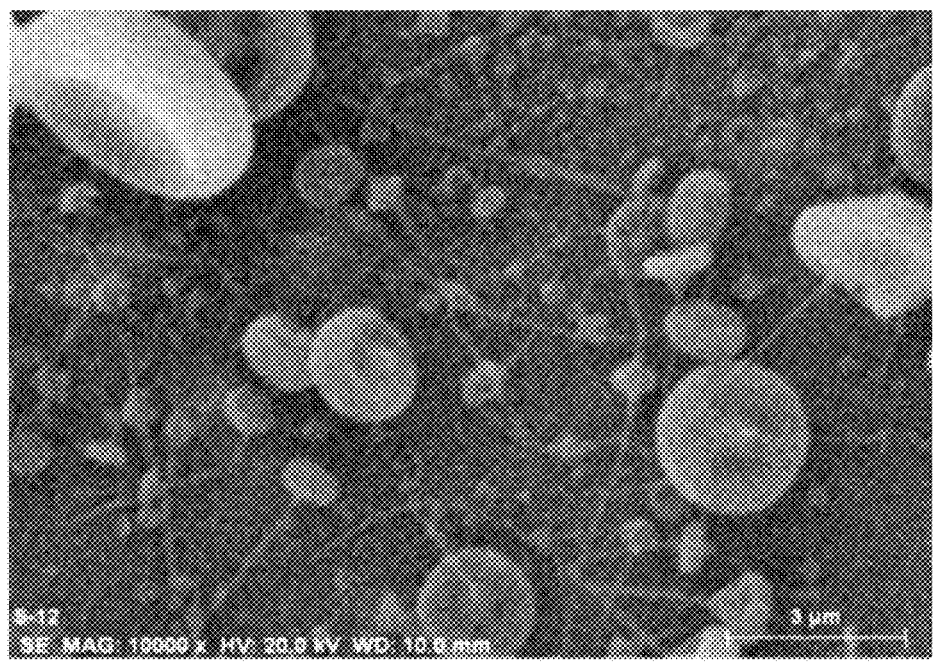
Figure 17(C): 3%PEA, 12%EC, 2%BSA

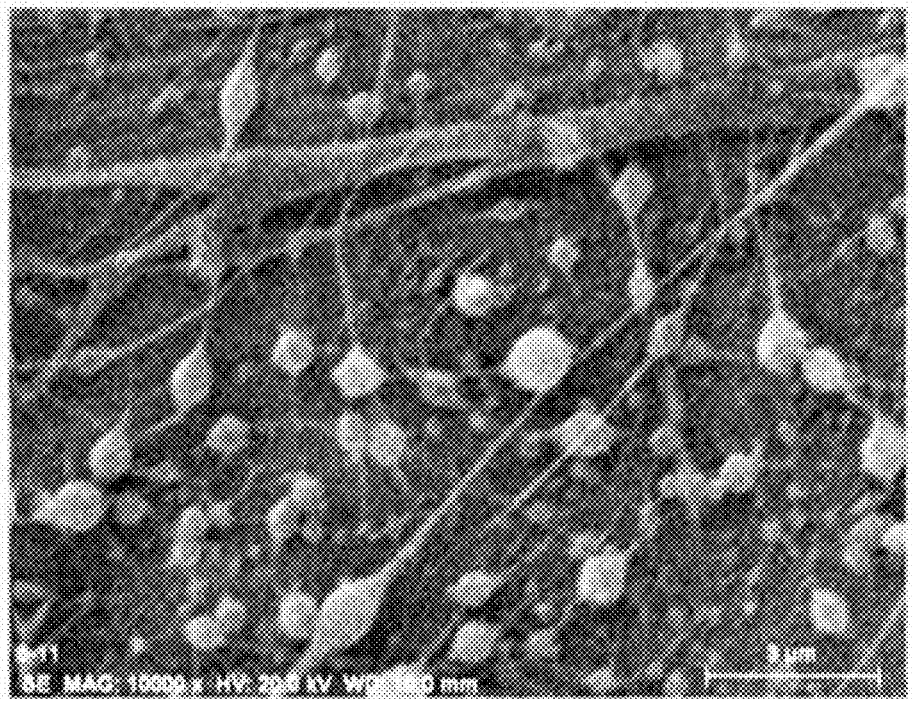
Figure 17(D): 3%PEA, 12%EC, 2%BSA with 10% triclosan

3%PEA/8%PLA/2%HSA
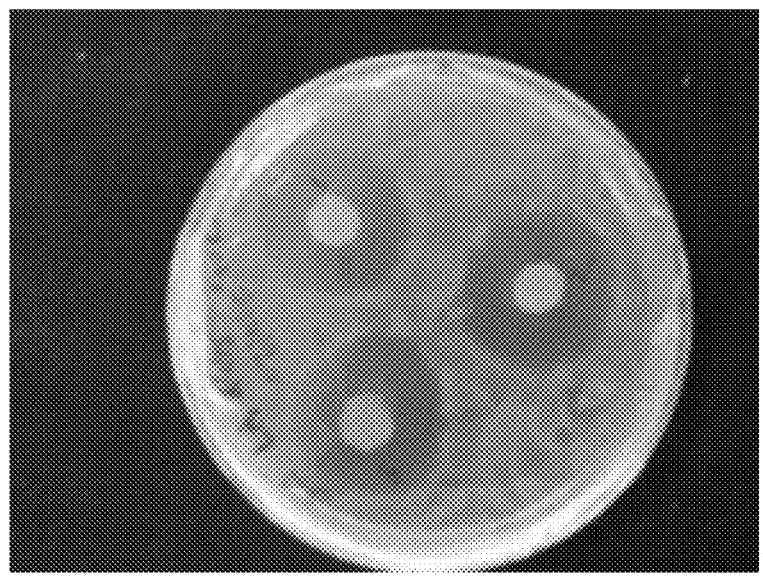
3%PEA/8%PLA/2%HSA with 10% Triclosan
Figure 18

BIOACTIVE OIL BASED POLYESTERAMIDE NANOFIBERS FOR WOUND HEALING APPLICATIONS

CROSS-REFERENCE TO RELATED APPLICATION

This application is a national phase entry of PCT/IN2015/000167, filed on 13 Apr. 2015, which claims the benefit of priority of Indian application No. 0088/DEL/2014 filed on 13 Apr. 2014, the contents of both of which as are incorporated herein by reference in their entirety for all purposes.

TECHNICAL FIELD

The present invention relates to bioactive oil based polyesteramide nanofibers. Particularly, the present invention relates to biocompatible and biodegradable nanofiber composition comprising oil based polyesteramide, a protein/polysaccharide, hydrophilic or hydrophobic polymer and a pharmaceutical; drug useful for wound healing and biomedical applications thereof.

BACKGROUND

Biocompatible and biodegradable nanofiber mats are finding increasing appeal in biomedical and bio-technological applications. They are attractive as vehicles for drug delivery—both immediate and controlled or sustained release. Several processes are available for synthesis of nanofiber mats such as drawing, phase separation and electrospinning. The latter is a method that is most amenable to mass production.

Most of the published electrospun absorbable fibrous products are fabricated from commercially available and well-established absorbable polymers from the synthetic aliphatic polyester family, such as polylactide (PLA), polyglycolide (PGA), polycaprolactone (PCL) and their co-polymers due to their commercial availability, degradability, biocompatibility, fiber-formation ability and mechanical property.

Polymer nanofibers are currently used in the treatment of wounds or burns of human skin, as well as are designed for haemostatic devices with unique characteristics which can let wounds heal by encouraging the formation of normal skin growth and eliminate the formation of scar tissue which otherwise occur in a traditional treatment. Non-woven nano-fibrous membrane mats for wound dressing usually have pore sizes ranging from 500 nm to 1 um, small enough to protect the wound from bacterial penetration via aerosol particle capturing mechanisms and possess high surface area of 5-100 $m^2/g$ which makes it extremely efficient for fluid absorption and dermal delivery.

Delivery of drug/pharmaceuticals to patients in the most physiologically acceptable manner has always been an important concern in medicine. In general, the smaller the dimensions of the drug and the coating material required to encapsulate the drug, the better the drug to be absorbed by human being. Drug delivery with polymer nanofibers is based on the principle that dissolution rate of a particulate drug increases with increasing surface area of both the drug and the corresponding carrier if needed. Kenawy et al. in Journal of Controlled Release 2002; 81:57-64 investigated delivery of tetracycline hydrochloride based on the fibrous delivery matrices of poly (ethylene-co-vinylacetate), poly (lactic acid), and their blend. In another work, bioabsorbable nanofiber membranes of poly (lactic acid) targeted for the prevention of surgery induced adhesions, were also used for loading an antibiotic drug, Mefoxin. As the drug and carrier materials can be mixed together for electro-spinning of nanofibers, the blend of drug and carrier materials integrated into one kind of fibers containing both components, and the carrier material is electrospun into a tubular form in which the drug particles are encapsulated.

Canadian Patent Publication No.: CA2161196, titled, "Polymeric Composition", discloses a polymeric composition for use in medicine which includes a hydrophobic bioabsorbable polymer admixed with a hydrophilic liquid polymer wherein the polymeric composition undergoes macroscopic phase separation on contact with aqueous media. The polymeric composition optionally includes a medicinal agent.

EP Publication No.: 2588659, titled, "Filament comprising an ingestible active agent non-woven web and method for making same", relates to a filament comprising a filament-forming material and an additive that is releasable and/or release from the filament for example when the filament is exposed to condition of intended use. The filaments may be hydrophilic or hydrophobic and is may be surface treated and/or internally treated to change the inherent hydrophilic or hydrophobic properties of the filament.

US Patent Publication No.: US20060024357, titled, "Wound healing polymer compositions and method for use thereof" describes wound healing compositions that can be fashioned into wound dressings, implants and surgical device coatings, which wound healing compositions comprise (a) a biodegradable, biocompatible polymer, a hydrogel, or both, as a carrier into which is dispersed, mixed, dissolved, homogenized, or covalently bound ("dispersed") (b) at least one wound healing agent. Optionally, additional bioactive agents can be dispersed within the polymer, hydrogel, or both.

Further, there is paper publication disclosed in International Conference on Advances in Polymeric Materials & Nanotechnology, Proceedings of Poly Tech—2012, titled 'Egg albumin based non-woven nanofiber scaffolds for tissue engineering' by Komal Pandey, Shubhang Agrawal et al. disclose composites of PCL/PLA/EA nanofiber scaffolds for tissue engineering.

Chinese Publication No.: CN102824641, titled "Two-phase drug-release multilayer drug-loaded nanofiber mat and preparation method thereof", relates to a two-phase drug-release multilayer drug-loaded nanofiber mat which consists of a water-soluble polymer, a water-insoluble polymer and a drug. The water-soluble polymer is polyvinyl pyrrolidone K30; water-insoluble polymer is ethyl cellulose and drug is ketoprofen.

Essential fatty acids have been used to reduce inflammation and promote wound healing in burn victims. Animal research indicates that omega-3 fatty acid helps to promote a healthy balance of proteins in the body which is important for recovery after sustaining a burn.

EA (Egg albumin) is a functional Globular Protein having beneficial properties for Polymer solution preparation. EA contributes to many parameters of electrospining as it increases the viscosity and conductivity (viscosity is inversely proportional to surface tension) of polymer solution. Pure EA protein is unable to produce nanofibers; even though the protein has sufficient polymer concentration, viscosity, conductivity and surface tension, since it lacked enough viscoelastic properties (GVN Rathna et al Polymer Journal (2011) 43, 654-661.

Hydroxybutyric acid-co-valeric acid (PHBV) is natural biodegradable polymers. PHBV possesses good biocompatibility and degrades in vivo into d-3-hydroxybutyric acid which is a normal constituent of human blood.

Since there remains a need in the art to provide biodegradable and biocompatible nanofibers composition for wound healing with better patient compliance, the present invention provides a novel biodegradable nanofiber composition using oil based biodegradable polymers by blending with hydrophobic and hydrophilic material for wound healing treatment and other biomedical applications.

Main object of the present invention is to provide bioactive oil based polyesteramide nanofibers.

Another object of the present invention is to provide a nanofiber composition comprising biodegradable and biocompatible hydrophobic polymer, hydrophilic polymer and polyesteramide of oil, useful for wound healing and biomedical applications.

SUMMARY

Accordingly, present invention provides a biocompatible and biodegradable nanofiber composition for wound healing and biomedical applications thereof comprising:
a. Hydrophobic polymer selected from the group consisting of polycaprolactone (PCL), polylactide, polyhydroxyalkonates, polyglycolide, 2-hydroxy ethyl cellulose or Poly(3-Hydroxy butyric acid co-3-valeric acid) (PHBV);
b. polysaccharides or proteins such as ethyl cellulose, egg albumin, bovine serum albumin (BSA) or human serum albumen;
c. polyesteramide of linseed, castor or neem oil optionally incorporated with a transition metal ion; and
d. optionally a pharmaceutical drug.

In an embodiment of the present invention, the hydrophobic polymer is present in an amount 0.1 to 20%.

In another embodiment of the present invention, the protein/polysaccharide are present in an amount 0.1 to 15%.

In yet another embodiment of the present invention, the polyesteramide of linseed, castor or neem oil is present in an amount 0.1 to 20%.

In yet another embodiment of the present invention, the pharmaceutical drug is in an amount of 5-22% w/w of the polymer.

In yet another embodiment of the present invention, thickness of the nanofibers is in the range 0.1 µm to 1 cm.

In yet another embodiment of the present invention, the nanofiber is in the form of mat, film or gel.

In yet another embodiment, of the present invention, the biocompatible and biodegradable nanofiber composition for wound healing and biomedical applications comprising:
a. polycaprolactone (PCL) in an amount of 0.1 to 20%;
b. egg albumin (EA) in an amount of 0.1 to 15%;
c. polyesteramide of linseed, castor or neem oil in an amount of 0.1 to 20% optionally incorporated with a transition metal ion.

In yet another embodiment of the present invention, the biocompatible and biodegradable nanofiber composition for wound healing and biomedical applications comprising;
a. poly (hydroxybutyric acid-co-valeric acid) (PHBV) in an amount of 0.1 to 20%;
b. egg albumin (EA) in an amount of 0.1 to 15%;
c. polyesteramide of linseed oil in an amount of 0.1 to 20% optionally incorporated with a transition metal ion.

In yet another embodiment of the present invention, pharmaceutical drug is selected from the group consisting of antibacterial agents, antimicrobial agents, antifungal agents, antibiotics such as amoxicillin, chlorhexidin digluconate, Cloxacillin, Dicloxacillin, Methicillin, Oxacillin, Cephalosporin, Penicillin G, Penicillin V, neomycin, Neosporin, Mupiricin, Gentamicin, Clotrimazole, Mafenide acetate/ nystatin, triclosan and such like.

In yet another embodiment, present invention provides a process for preparation of a biocompatible and biodegradable nanofiber composition for wound healing and biomedical applications thereof comprising the steps of:
i. preparing a blend of hydrophobic moiety polymer selected from polycaprolactone, polylactide, polyhydroxyalkonates, polyglycolide, Poly(3-Hydroxy butyric acid co-3-Valeric acid; polysaccharides or proteins such as ethyl cellulose, egg albumin or Bovine Serum albumin (BSA) and polyesteramide of linseed, neem of castor oil optionally incorporated with a transition metal ion and optionally with pharmaceutical drug;
ii. electrospinning the blend of step (a) to obtain nano-sized fibers; and
iii. crosslinking the nanofibers obtained in step (b) by annealing at a temperature in the range of 50-100° C. to obtain crosslinked nanofiber mats or films or gel.

In yet another embodiment, present invention provides a method of treating the subject with burns, acne, lesions, injuries, cuts, wounds and such like comprising applying the biocompatible and biodegradable nanofiber composition comprising; (a) Hydrophobic polymer selected from polycaprolactone, polylactide, polyhydroxyalkonates, polyglycolide, Poly(3-Hydroxy butyric acid co-3-valeric acid); (b) polysaccharides or proteins such as ethyl, cellulose, egg albumin Bovine Serum albumin (BSA) or human serum albumin (HAS); and (c) polyesteramide of linseed, castor or neem oil optionally incorporated with a transition metal ion; and (d) optionally a pharmaceutical to the affected area.

In yet another embodiment, said composition is useful in the treatment of burns, acne, lesions, injuries, cuts, wounds and such like to the subject in need thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6: NMR of Fe-PEA.

FIG. 11: A—SEM images of 1% PHBV+2% EA+7% PEA(S-1),
B—SEM image of 2% PHBV+2% EA+7% PEA(S-2),
C—SEM image of 3% PHBV+2% EA+5% PEA(S-3),
D—SEM image of 4% PHBV+2% EA+6% PEA(S-4),
E—SEM image of 5% PHBV+2% EA+3% PEA(S-5)
FIG. 12: F: Crosslinked SEM image of 5% PHBV+2% EA+3% PEA Without drug (S-5),
G: Crosslinked SEM image of 5% PHBV+2% EA+3% PEA+10% Drug (S-7),
H: Crosslinked SEM image of 5% PHBV+2% EA+3% PEA+15% Drug (S-8),
I: Crosslinked SEM image of 5% PHBV+2% EA+3% PEA+20% Drug (S-9).
FIG. 13: Antibacterial study of 10%, 20% and 30% of PEA, Zn-PEA and Fe-PEA against S. aureus.
FIG. 16: The calibration curve of drug, chlorhexidine.
FIG. 17: SEM images of 3% PEA, 8% PLA, 2% HSA (A), 3% PEA, 8% PLA, 2% HSA with 10% triclosan (B) and 3% PEA, 12% EC, 2% BSA (C) and 3% PEA, 12% EC, 2% BSA with 10% triclosan (polymer to drug ratio).
FIG. 18: Antibacterial properties of 3% PEA, 8% PLA, 2% HSA with and without Triclosan.

ABBREVIATIONS

Figure 1:
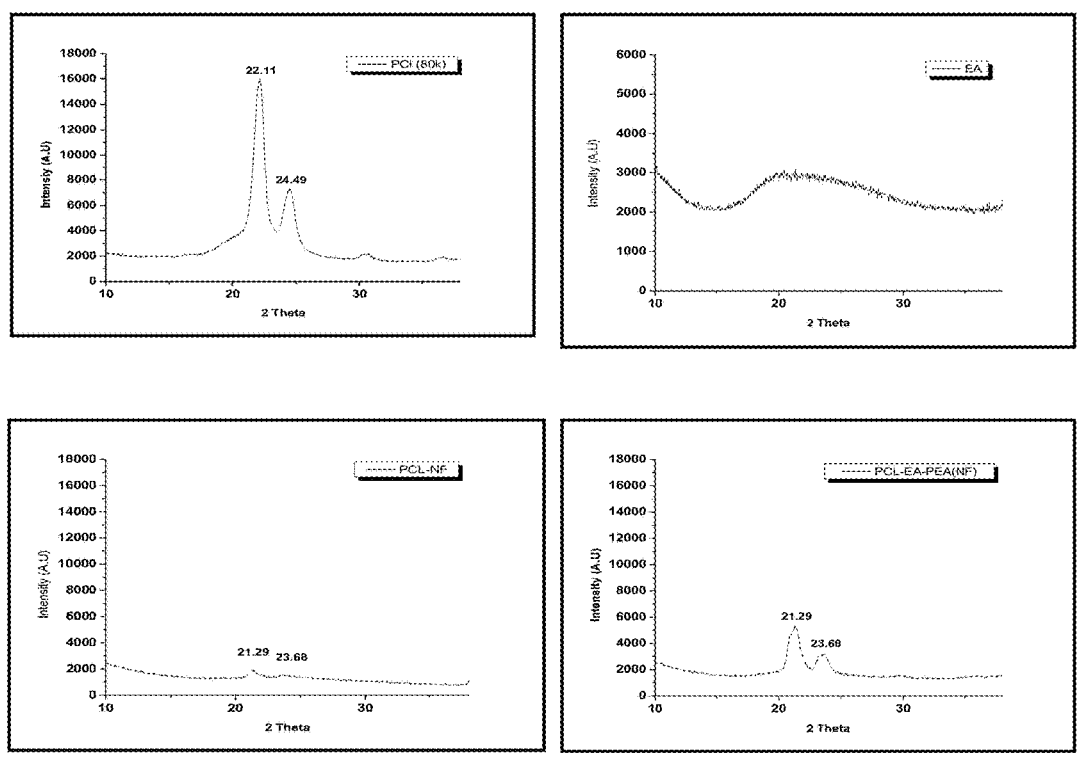
FIG. 1: WXRD of pure PCL, EA, PCL nanofiber and PCL/EA/PEA nanofiber.

PCL: Polycaprolactone
EA: Egg albumin
PEA: Polyester amides
BSA: Bovine Serum albumin
HSA: Human serum albumen
EC: Ethyl cellulose
NNF: Neem oil Based Polyesteramide drug loaded nanofiber
LNF: Linseed oil Based Polyesteramide drug loaded nanofiber
CNF: Castor oil Based Polyesteramide drug loaded nanofiber
Zn-PEA: Zinc-Polyesteramide
Fe-PEA: Ferrous-Polyesteramide
Zn-NPEA: Zinc-Neem Polyesteramide
PHBV: Polyhydroxybutyric acid-co-valeric acid
ALA: Alpha-linolenic acid
HELA: Hydroxyethyl linseed amide
Amox: amoxicilline

DETAILED DESCRIPTION

The inventors propose non-woven nanofibers by using oil based biodegradable polymers such as polyesteramide of oil by blending with protein/polysaccharide and hydrophobic polymer for wound healing and biomedical applications.

Present invention provides biocompatible and biodegradable nanofiber composition for wound healing and biomedical applications thereof comprising:
a. hydrophobic moiety independently selected from polycaprolactone, polylactide, polyhydroxyalkonates, polyglycolide, poly (hydroxybutyric acid-co-valeric acid (PHBV);
b. hydrophilic/hydrophobic moiety selected from polysaccharide or proteins such as egg albumin or Bovine Serum albumin (BSA), human Serum albumin (HSA) or ethyl cellulose (EC);
c. polyesteramide of linseed, castor or neem oil optionally incorporated with a transition metal ion.

The nanofibers of the present invention are further cross-linked by annealing to obtain mats, films or gels.

The nanofiber optionally comprises a pharmaceutical drug in an amount of 18-22% w/w of the polymer and is selected from antibacterial agents, antimicrobial agents, antifungal agents, antibiotics such as amoxicillin, chlorhexidin digluconate, Cloxacillin, Dicloxacillin, Methicillin, Oxacillin, Cephalosporin, Penicillin G, Penicillin V, neomycin, Neosporin, Mupiricin, Gentamicin, Clotrimazole, Mafenide acetate/nystatin, triclosan and such like.

The polysaccharides or proteins are present in an amount in the range 0.1 to 20% of the total composition.

The hydrophobic polymer is present in an amount of 0.1 to 15% of the total composition.

The polyesteramide of linseed, castor or neem oil is present in an amount of 0.1 to 20% of the total composition.

The ratio of hydropilic or hydrophobic polysaccharide or protein moiety:hydrophobic polymer:polyesteramide is 0.1 to 15%:0.1 to 20%:0.1 to 20%.

Present invention provides biocompatible and biodegradable nanofibers composition comprising polycaprolactone (PCL) in an amount of 0.1 to 20%; egg albumin in an amount of 0.1 to 15%; and polyesteramide of linseed, castor or neem oil in an amount of 0.1 to 20%; optionally incorporated with a transition metal ion. The nanofiber may further comprise a pharmaceutical drug.

Present invention provides biocompatible and biodegradable nanofiber composition for wound healing and biomedical applications comprising poly (hydroxybutyric acid-co-valeric acid) (PHBV) in an amount of 0.1 to 20%; egg albumin (EA) in an amount of 0.1 to 15%; polyesteramide of linseed oil in an amount of 0.1 to 20% optionally incorporated with a transition metal ion. The nanofiber may further comprise a pharmaceutical drug.

the present invention relates to a biocompatible and biodegradable nanofiber composition for wound healing and biomedical applications thereof comprising poly (hydroxybutyric acid-co-valeric acid) (PHBV) in an amount of 0.1 to 20%; egg albumin (EA) in an amount of 0.1 to 15% polyesteramide of linseed oil optionally incorporated with a transition metal ion such as Fe or Zn and optionally pharmaceutical drug.

The present invention provides process for synthesis of nanofiber composition for wound healing and other biomedical application comprising preparing blend of hydrophobic polymer, hydrophilic or hydrophobic polymer, protein/polysaccharide and polyesteramide of linseed, castor or neem oil optionally containing a transition metal ion by electrospinning method known in the art. The non-woven nanofibers obtained are further crosslinked by heating to a temperature in the range of 50-100° C. to obtain crosslinked mats, films or gels.

The present invention provides drug loaded nanofiber composition useful for wound healing and biomedical application thereof comprising:
i. hydrophobic polymer selected from polycaprolactone, polylactide, polyhydroxyalkonates, polyglycolide, or poly (3-hydroxy butyric acid co-3-valeric acid);
ii. hydrophilic/hydrophobic polymer selected from polysaccharides or proteins such as egg albumin or bovine serum albumin (BSA) or human serum albumen (HAS) or ethyl cellulose;
iii. polyesteramide (PEA) of linseed, castor or neem oil optionally containing transition metal ion; and optionally
iv. a pharmaceutical drug.

The nanofiber composition of the present invention can be in the form of films, mats or gels. The thickness of nanofiber is from 0.1 μm to 1 cm.

The present invention relates to a biocompatible and biodegradable nanofiber composition for wound healing and biomedical applications thereof comprising 3% PEA, 8% PLA, 2% HSA and optionally a pharmaceutical drug.

The present invention relates to a biocompatible and biodegradable nanofiber composition for wound healing and biomedical applications thereof comprising 3% PEA, 12% EC, and 2% BSA and optionally a pharmaceutical drug.

The present invention relates to process for preparation of nanofiber composition comprising:
a) preparing a blend of hydrophobic polymer selected from polycaprolactone, polylactide, polyhydroxyalkonates, polyglycolide or Poly(3-Hydroxy butyric acid co-3-Valeric acid, hydrophilic or hydrophobic, polysaccharides or proteins such as ethyl cellulose, egg albumin or Bovine Serum albumin (BSA) or human serum albumen (HAS) and polyesteramide of linseed, neem or castor oil optionally incorporated with a transition metal ion and optionally with a pharmaceutical drug;
b) electrospinning the blend of step (a) to obtain nano-sized fibers; and
c) crosslinking the nanofibers obtained, in step (b) by annealing at a temperature in the range of 50-100° C. to obtain crosslinked nanofiber mats or films or gel.

The nanofibers are characterized and analyzed by SEM (Scanning Electron Microscopy), FT-IR (Fourier transform infrared), DSC (Differential Scanning Calorimetry), XRD (X-ray Diffractometry).

In another embodiment, the present inventions relates to process for preparation of biocompatible and biodegradable nanofiber composition for wound healing and biomedical applications thereof comprising preparing a blend of hydrophobic polymer selected from polycaprolactone (PCL), hydrophilic moiety selected from egg albumin (EA) and polyesteramide of neem, linseed or castor oil and electrospinning by a method known in the art to obtain nano-sized fibers and further annealing at a temperature in the range of 50-100° C. to obtain crosslinked nanofiber mats, films or gels.

Accordingly, weighed amount of PCL is dissolved in formic acid until complete dissolution of PCL to obtain transparent viscous solution. To the viscous solution is added PEA (Neem, Linseed, Castor oil based) and vortexed, followed by the addition of EA solution prepared in formic acid at room temperature. The solution mixture is further vortexed to attain complete dissolution. Various compositions prepared are listed in Table 1. The solution was subjected to electrospining to produce nanofibers.

In yet another preferred embodiment, the present inventions relates to process for preparation of biocompatible and biodegradable nanofiber composition for wound healing and biomedical applications thereof comprising preparing a blend of hydrophobic moiety selected from Poly(3-Hydroxy butyric acid co-3-Valeric acid), hydrophilic moiety selected from egg albumin (EA) and polyesteramide (PEA) of linseed oil containing transition metal ion such as Fe or Zn and electrospinning by a method known in the art to obtain nano-sized fibers and further annealing at a temperature in the range of 50-100° C. to obtain crosslinked nanofiber mats, films or gel.

The process for preparation of Fe-PEA or Zn-PEA includes the following steps:
i. preparing N, N-bis (2-hydroxyethyl) linseed amide (HELA) from linseed oil by the known method;
ii. refluxing the mixture of HELA dissolved in hydrocarbon solvent and phthalic anhydride under inert atmosphere till completion of reaction to obtain polyesteramide;
iii. optionally adding transition metal salt to the above reaction to obtain M-PEA (wherein 'M' is a transition metal ion).

Accordingly, mixture of linseed oil and diethanolamine are refluxed at a temperature in the range of 110-118° C. under nitrogen atmosphere and the progress of reaction was monitored by TLC using 30% ethyl acetate in PET ether. After completion of the reaction, is added diethyl ether and washed with 15% NaCl solution, the organic layer is dried and concentrated to obtain HELA.

To the solution of HELA dissolved in hydrocarbon solvent selected from toluene, xylene, benzene or higher aliphatic hydrocarbons is added to phthalic anhydride and refluxed under nitrogen atmosphere. The progress of reaction was monitored with TLC using 30% ethyl acetate in pet ether. The reaction mixture was diluted with hydrocarbon solvent, filtered and concentrated to obtain PEA.

Further, the preparation of Zn-PEA or Fe-PEA includes adding to the mixture of HELA dissolved in the hydrocarbon solvent and phthalic anhydride with equivalent amount of transition metal salt such as zinc acetate or ferrous hydroxide and refluxing the mixture at a temperature in the range of 65-120° C. until completion of the reaction monitored by TLC using 30% ethyl acetate in pet ether. The reaction mixture was diluted with hydrocarbon solvent, filtered and concentrated to obtain Zn-PEA or Fe-PEA respectively.

The process for preparing the blend of PHBV+EA+Zn-PEA or PHBV+EA+Fe-PEA includes dissolving the blend in HFIP and electrospinning at 15 KV to obtain the nanofiber. The concentration of PHBV is used in the range of 4-5% since above 5% PHBV is insoluble in HFIP. Compositions of solution blends used for Electrospinning is given in Table 4 below.

The nanofibers are crosslinked by annealing at a temperature in the range of 55-65° C. to obtain crosslinked nanofiber mats, films or gels.

The preparation of drug loaded nanofiber comprises adding variable concentration of pharmaceutical drug to the blend of hydrophobic moiety, polysaccharide/protein and polyesteramide of linseed, castor or neem oil optionally containing transition metal ion of specific concentration and electrospinning to obtain drug loaded nanofibers. The composition for solution blend with addition of drug used for electrospinning is shown in Table 5 below.

The present invention discloses drug loaded nanofiber mat useful for wound healing and biomedical application thereof comprising;
i. hydrophobic polymer selected from polycaprolactone, polylactide, polyhydroxyalkonates, polyglycolide or Poly (3-Hydroxy butyric acid co-3-Valeric acid);
ii. polysaccharides or proteins such as ethyl cellulose, egg albumin or Bovine Serum albumin (BSA) or human serum albumen (HSA);
iii. polyesteramide (PEA) of linseed, castor or neem oil optionally containing transition metal ion; and
iv. pharmaceutical drug.

The pharmaceutical drug is selected from antibacterial agents, antimicrobial agents, antifungal agents, antibiotics such as amoxicillin, chlorhexidin digluconate, Cloxacillin, Dicloxacillin, Methicillin, Oxacillin, Cephalosporin, Penicillin G, Penicillin V, neomycin, Neosporin, Mupiricin, Gentamicin, Clotrimazole, Mafenide acetate/nystatin, triclosan and such like. The drug is loaded in to the nanofiber composite in an amount of 5-22% w/w of the polymer.

Figure 3:
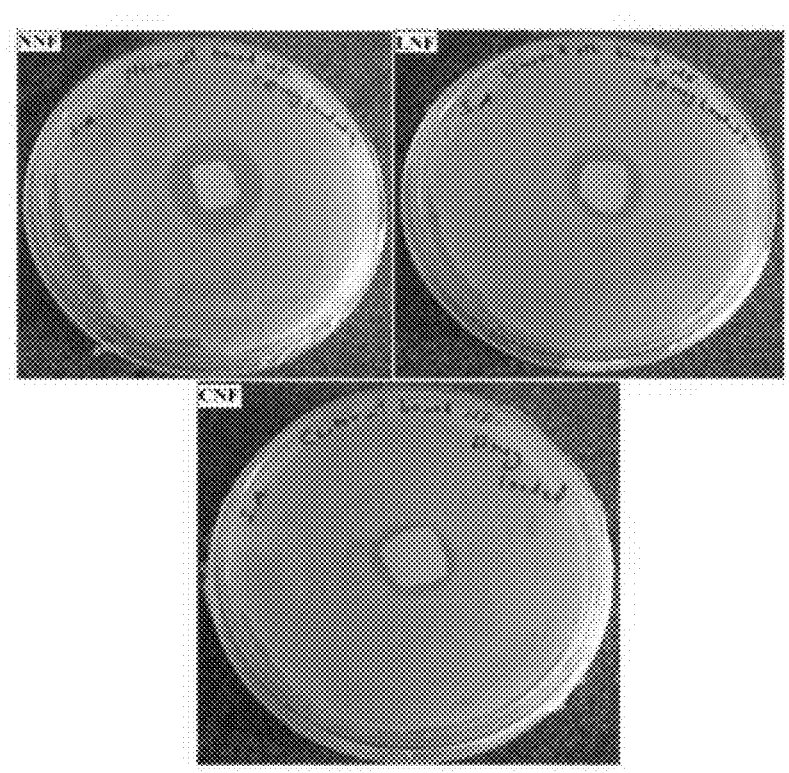
FIG. 3: Antibacterial activity of different drug loaded formulation of nanofiber mats NNF, LNF and CNF.

In an embodiment, the present invention discloses antimicrobial activity of the nanofibers containing amoxicillin against *Staphylococcus aureus*. The drug loaded nanofiber mat shows clear zone of inhibition based on the drug activity against the susceptible bacteria (FIG. 3). The minimum inhibitory concentration of Amoxacillin is in the range of 0.05 to 8 µg/ml.

Further, the antimicrobial activity of synthesized PEA, Zn-PEA, Fe-PEA and drug (chlorhexidin digluconate) was tested against *staphylococcus aureus* (gram-positive bacteria) and *Escherichia-coli* (gram-negative bacteria)

The present invention relates to method of treating the subject with burns, acne, lesions, injuries, cuts, wounds and such like comprising, applying the nanofiber mat of present invention to the affected area.

The present invention relates to the use of the nanofiber mat of present invention for treating burns, acne, lesions, injuries, cuts, wounds and such like to the subject in need thereof.

EXAMPLES

Following examples are given by way of illustration and therefore should not be construed to limit the scope of the invention.

Materials

Linseed oil, neem oil from Analab fine chemicals Mumbai India, diethanolamine from Merck Mumbai, India, Castrol oil and formic acid from Loba chemicals, Mumbai, India Ethyl acetate, Pet ether, analytical grade, India. PHBV from Good fellow cambridge limited, England. HAS, BSA, triclosan, PLA and PCL from Aldrich chemicals, Mumbai, India. HFIP from Merck, Germany. Zinc acetate and phthalic anhydride from S.D. fine chemicals, Mumbai, India. Formic acid from Thomas beaker chemicals, Mumbai, India. Chloroform from Merck, Mumbai, India. EA from Otto, Mumbai, India. Amoxicillin trihydrate was obtained as a gift sample from Micro labs limited, Bangalore, India. Sd fine chemicals Mumbai India, HFIP from Merck Mumbai India, Ferrous sulfate, Merck, Mumbai, India. Xylene from Rankem, India Chlorhexidin digluconate (20% in water) from Sigma Aldrich, nutrient agar, bacterial cultures of *Staphylococcus aureus* and *Escherichia coli* from NCIM, NCL, Pune.

Example 1

Electro Spinning Setup

A 10 ml of plastic syringe containing 5 ml of blend solution, and a stainless steel needle of diameter 0.8 mm attached to mouth of syringe, was assembled on a syringe pump. The needle was connected to high voltage generator, operating in positive DC mode at 14 kv. The distance between Needle tip to collector metal plate covered with an aluminium foil was maintained to 10 cm and the solution flow rate was controlled at 0.5 ml/hr by the syringe pump. The electrospuned nanofibers were collected on aluminum foil and kept for solvent evaporation at room temperature.

Electrospining of Pure PCL and PCL/EA/NPEA, LPEA, CPEA Blend

A weighed amount of PCL was dissolved in formic acid at 45 C.° after complete dissolution of PCL a transparent viscous solution was obtained. To this solution PEA (Neem, Linseed, Castor oil based) was added and vortexed, followed by addition of EA solution prepared in formic acid at room temperature. This solution mixture was further vortexed to attain complete dissolution. The various compositions that were prepared are listed in Table 1. The solutions were subjected to electrospining to produce nanofibers.

TABLE 1

Composition of solution of PCL/EA/PEA with drug or without drug for Electrospining:-

| Sr. No. | PCL (%) | EA (%) | PEA (%) | Drug (%) | Formulation code |
|---|---|---|---|---|---|
| 1. | 15 | 2 | 8 | 0 | B |
| 2. | 15 | 3 | 7 | 0 | C |
| 3. | 15 | 4 | 6 | 0 | D |
| 4. | 15 | 5 | 5 | 0 | E |
| 5. | 15 | 6 | 4 | 0 | F |
| 6. | 15 | 0 | 0 | 0 | A |
| 7. | 15 | 5 | 5 (NPEA) | 20 | NNF |
| 8. | 15 | 5 | 5 (LPEA) | 20 | LNF |
| 9. | 15 | 5 | 5 (CPEA) | 20 | CNF |

TABLE 2

Drug loading efficiency

| Formulation | Composition | Drug % w/w of Polymer | Estimated amount/Loaded amount (mg) |
|---|---|---|---|
| NNF 20 | PCL + EA + NPEA + Drug | 20 | 1.4/2 |
| LNF 20 | PCL + EA + LPEA + Drug | 20 | 1.25/2 |
| CNF 20 | PCL + EA + CPEA + Drug | 20 | 1.19/2 |

Crosslinking of Nanofiber

Crosslinking was done by annealing the nanofiber mats at 55° C. for 4 h. EA has sulfhydrl groups which on heating forms disulfide crosslinks. The E-SEM image shows the crosslinking of nanofiber mat in order to stick nanofibers to each other.

Example 2

Wide Angle X-Ray Diffraction

X-ray diffractogram were recorded for PCL pure, EA Pure, PCL nanofiber and PCL/EA/PEA nanofibers. The respective X-ray diffractogram are shown in FIG. 1. These studies were done to investigate the crystallinity of the polymers before and after electrospinning. PCL are semicrystalline and hence show to peaks at 2θ of 22.11° and 24.49°. However, the XRD of PCL nanofibers showed two low intensity peaks near about at same angle because during electrospining the polymer reduce crystalline nature due to limited time for the arrangement of molecules in regular form. EA did not show any crystalline peaks being amorphous. However, the PCL present in the nanofiber of blend, PCL/EA/PEA was confirmed due to the presence of peaks at 2θ of 21.29° and 23.68° which are same as the PCL nanofiber diffractogram.

Fourier Transforms Infrared (FTIR) Spectroscopy

Figure 2:
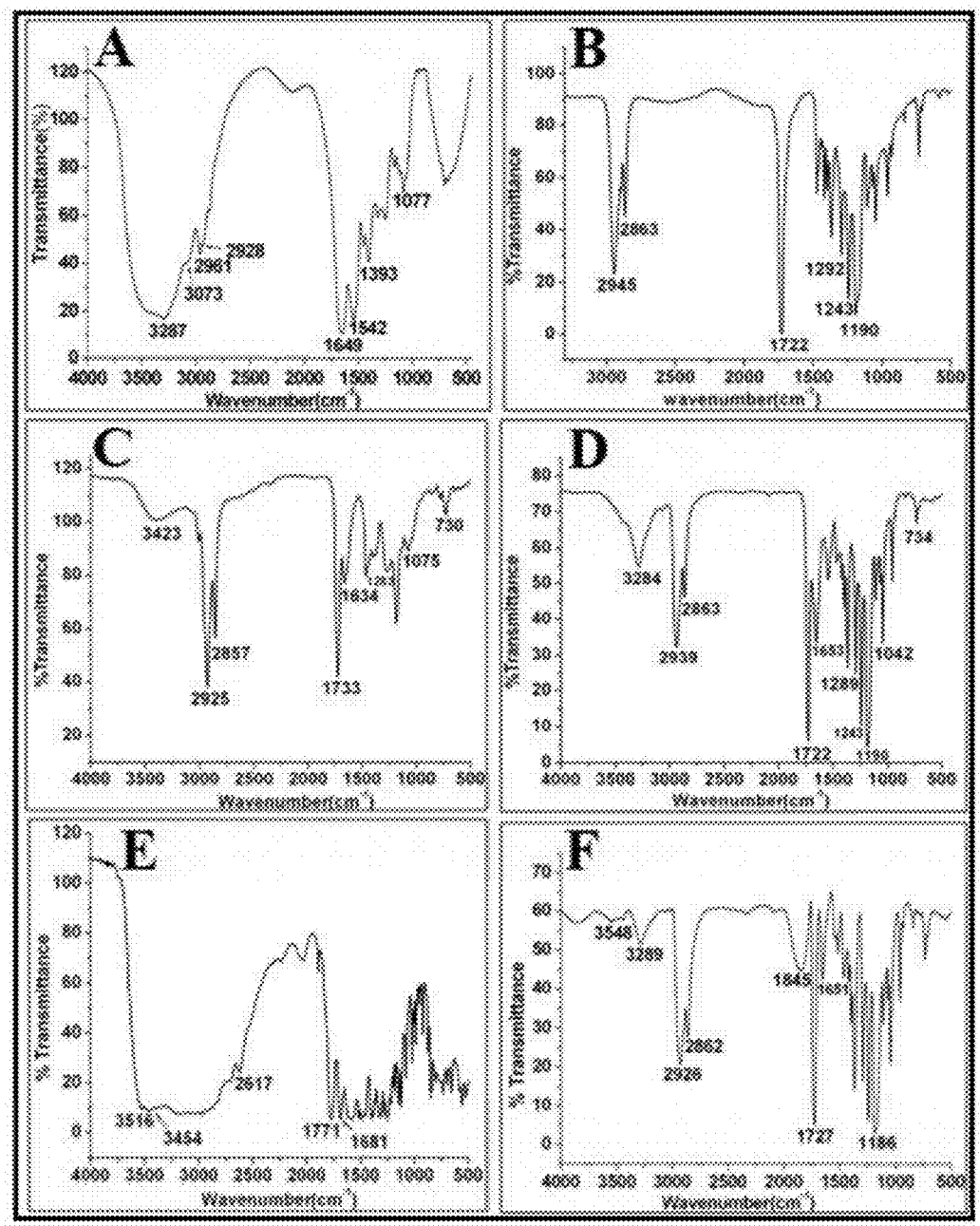
FIG. 2: FTIR Spectra of EA (A), PCL (B), Pure PEA (C), nanofiber mat of blend PCL/EA/PEA (D), Amoxicilline (E) and nanofiber mat of blend PCL/EA/PEA with Amox (F).

The developed nanofibers were characterized by FTIR to identify functional groups and the presence of the polymers in the prepared blends. FIG. 2 shows the Infrared absorption spectra for pure EA (A), PCL (B), Pure PEA (C), nanofiber mat of blend PCL/EA/PEA (D), Amoxicillin (E) and nanofiber mat of blend PCL/EA/PEA with drug (F). FIG. 2 A shows characteristic peaks at 3287 $cm^{-1}$, 3073 $cm^{-1}$ due to —NH stretching of the secondary amide and 1542 $cm^{-1}$ typical for amides and amines, major functional groups of many proteins also the spectra shows —C=O stretching at 1649 $cm^{-1}$ (amide-I) and —NH bending at 1542 $cm^{-1}$ (amide II), —CH stretching at 2961 $cm^{-1}$ and a weak peak at 2928 $cm^{-1}$ due to —SH stretching present in EA (7). PCL pure (FIG. B) shows characteristic peak at 2945 $cm^{-1}$ and 2863 $cm^{-1}$ which is due to asymmetric and symmetric CH2 stretching, 1722 $cm^{-1}$ due to carbonyl stretching(C=O). PCL also gives 1293 $cm^{-1}$ due to C—O and C—C stretching in the crystalline phase: Zinc incorporated polyesteramide (PEA) (FIG. C) shows characteristics peaks at 3423 $cm^{-1}$ due to alcoholic OH group, 1075 $cm^{-1}$ due to primary alcohol, 1723 $cm^{-1}$ due to ester group, 1634 $cm^{-1}$ due to amide groups. Polyesteramide also shows stretching at 2857 $cm^{-1}$ and 2925 $cm^{-1}$ due to $CH_2$ symmetric and asymmetric groups (3). The pure amox (FIG. E) spectra shows —OH stretching between 3454-3516 $cm^{-1}$, a peak at 1771 $cm^{-1}$ indicates β-lactum —C=O stretching present in amox which is responsible for an bacterial activity of drug. The presence of —C=O (amide-I) stretching indicated by the peak at 1688 $cm^{-1}$. The PEA/EA/PEA blend spectra shown by FIG. D that indicated the respective peaks of PCL,EA and PEA with merging and shifting in the spectra. The FT-IR spectra of the blends of nanofiber with and without Amox has shown by FIG. F which revealed the characteristic peaks of all the polymers indicating that the drug, amox and all the polymer were used to develop the nanofiber mats is blended properly. The merging and shifting of the bands to higher frequency has indicated that hydrogen ion interactions occurred between the polymers and the drug. On the basis of this spectrum we conclude that PEA/PCL/EA and the amox properly incorporated in nanofiber.

Example 3

In-Vitro Release Study

Total immersion method was used for studying the cumulative release profiles of amoxicillin from drug-loaded nanofiber mats. The respective nanofiber mats 5 mg were first placed in Screw cap tube containing 35 ml of pH 7.4 phosphate buffer solution (PBS) maintained 37° C. at 50 rotation/min in a thermostatical shaking incubator. At intervals, 2 ml samples were taken from the buffer solution and replaced the sampling with 2 ml fresh buffer solution which was maintained at 37° C. The amount of amoxicillin present in the buffer sample was determined by a UV-Visible spectrophotometer at the wavelength of 272 nm. A blank film of the blend without amoxicillin was used as the control.

The results were presented in terms of cumulative % release as a function of release time. The equation 1 shows the method for obtaining the cumulative % release.

$$\text{Cumulative \% release} = M_t/M_\infty \times 100\%$$

Figure 4:
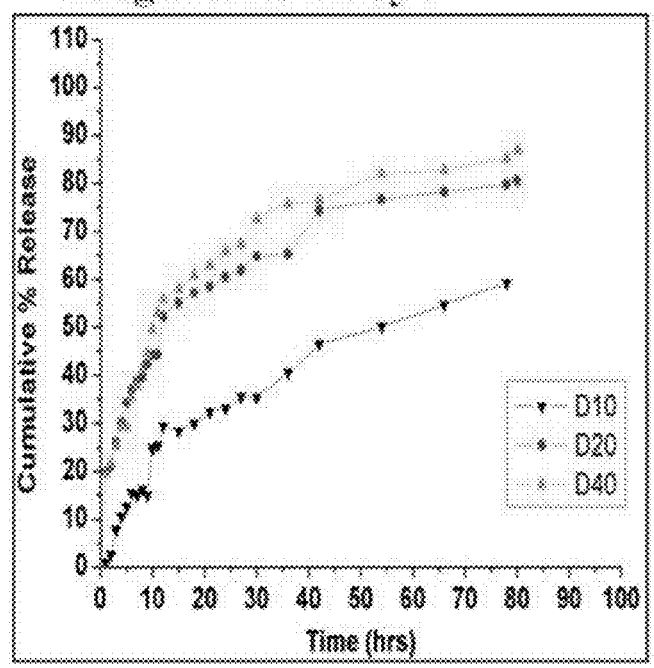
FIG. 4: Drug release profile of formulation NNF. The drug release studies were done in phosphate buffer saline of pH 7.4 at 37±0.5° C. in a thermostatically shaking incubator. The drug from the nanofibers mat is released with slightly increasing in manner; about 93% drug is released within 90-95 hours from nanofibers mat. 10% drug loaded nanofibers shows initial 30% release in 12 h followed by 50% release during 80 h. 20% and 40% drug loaded nanofibers shows 80-85% drug release during 80 h.
Figure 7:
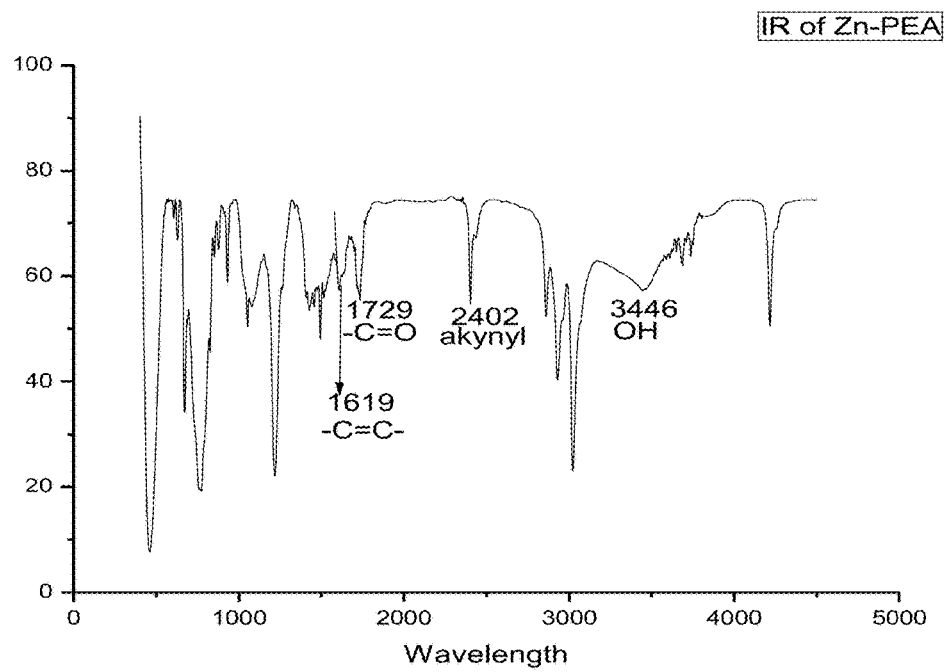
FIG. 7: IR of Zn-PEA.
Figure 8:
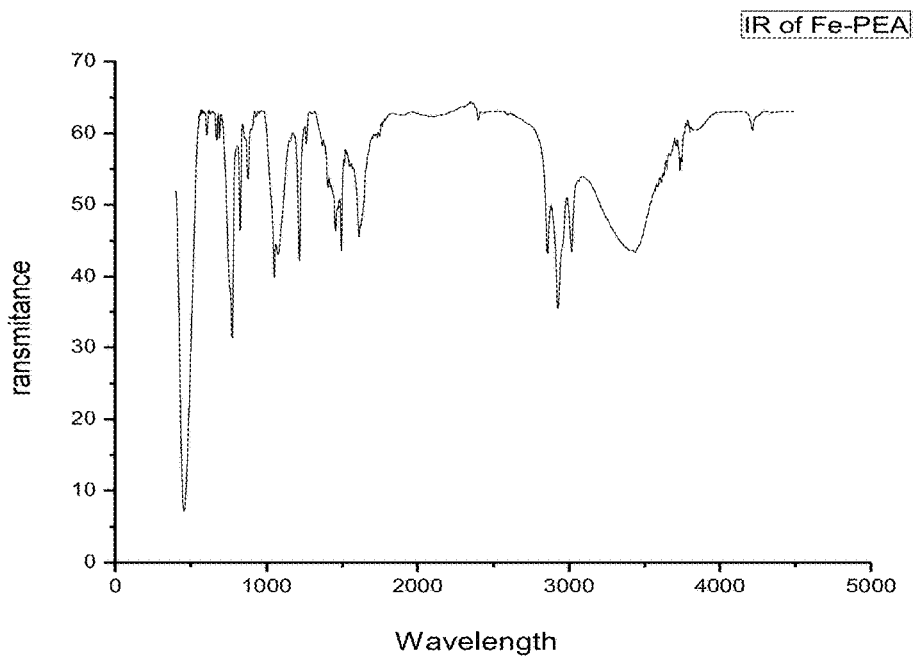
FIG. 8: IR of Fe-PEA.
Figure 9:
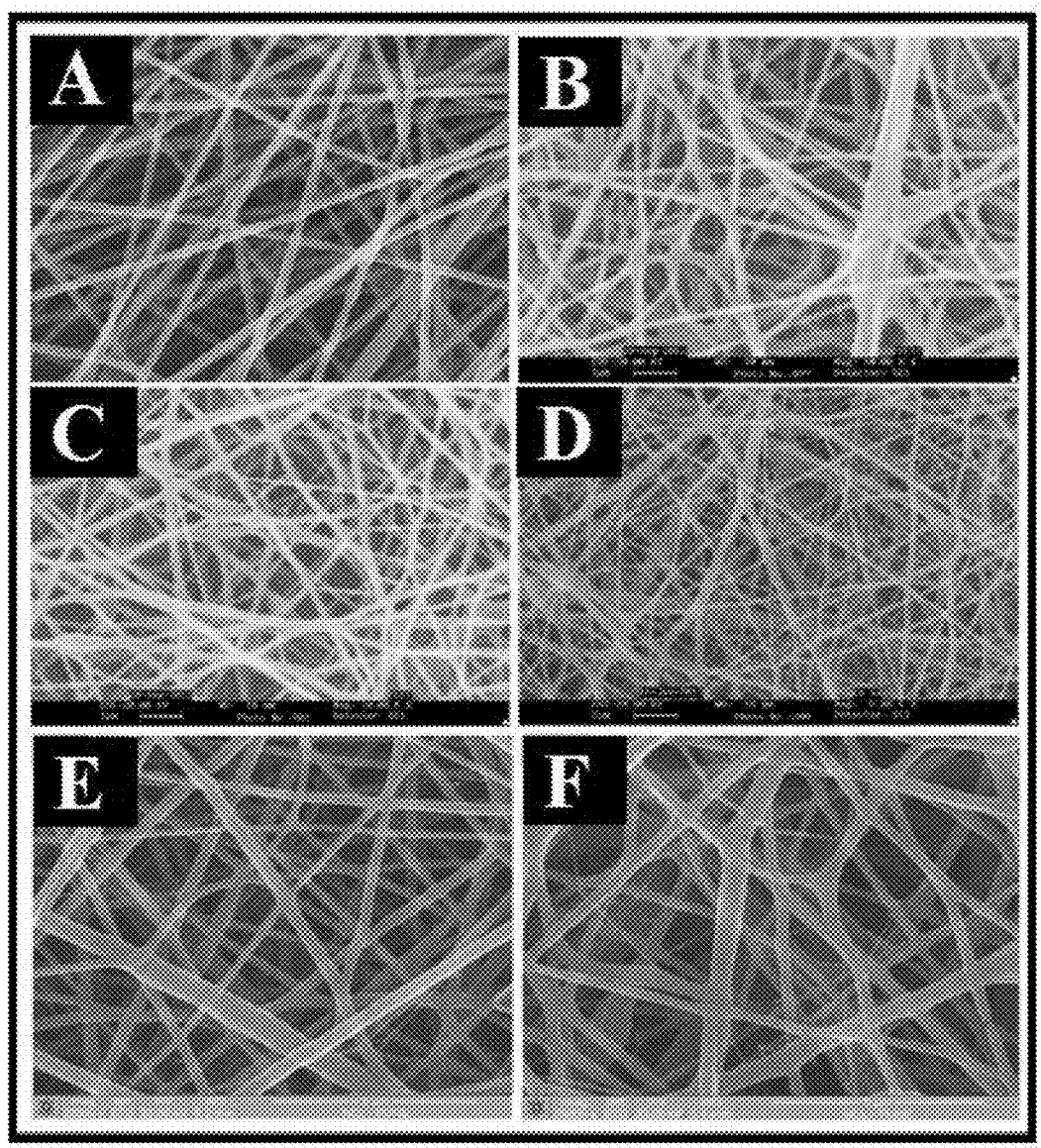
FIG. 9: A—SEM images of 15% PCL,
B—SEM images of 15% PCL/2% EA/8% PEA,
C—SEM images of 15% PCL/3% EA/7% PEA,
D—SEM images of 15% PCL/4% EA/6% PEA,
E—SEM images of 15% PCL/5% EA/5% PEA.
F—SEM images of 15% PCL/6% EA/4% PEA.
Figure 10:
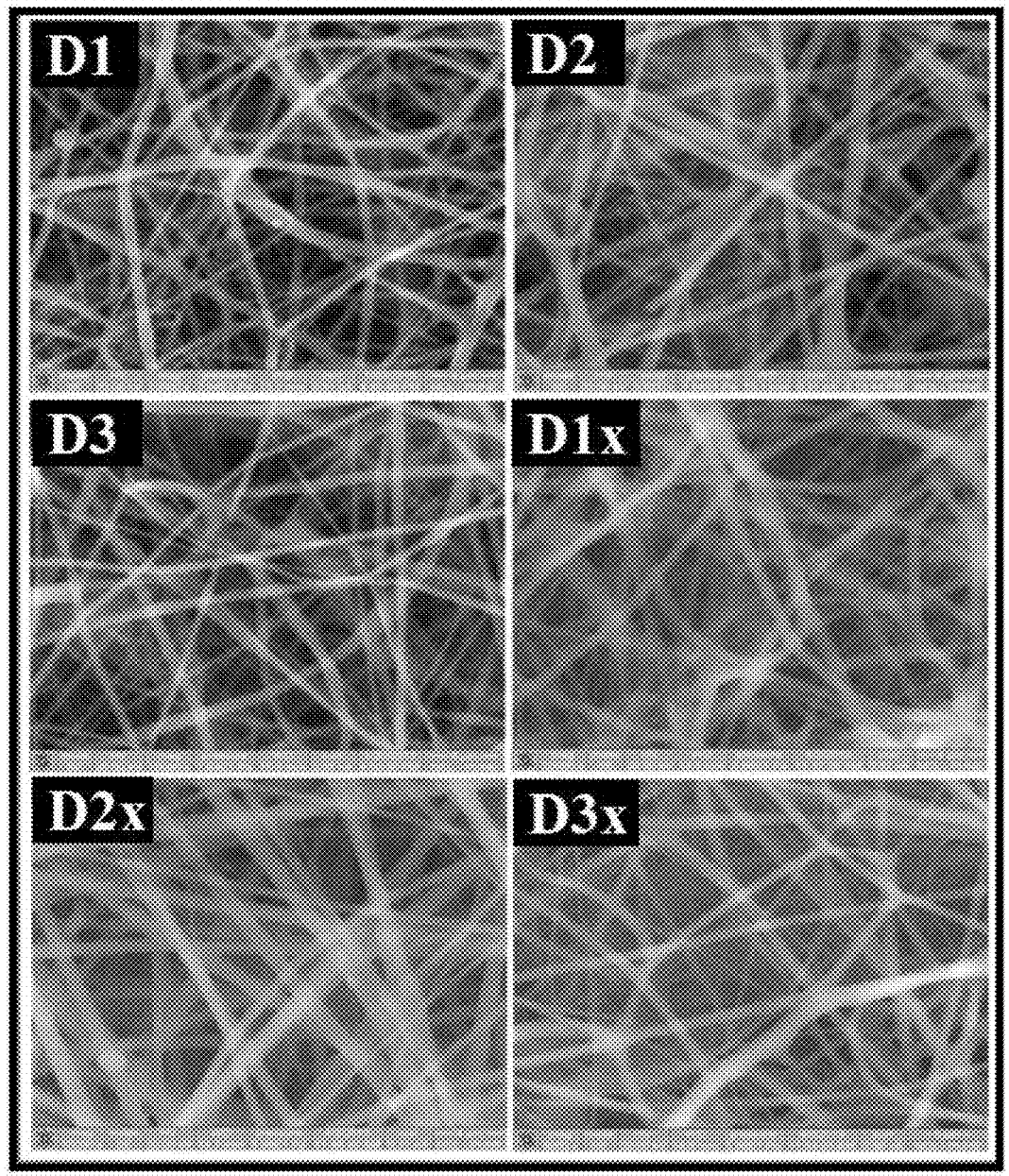
FIG. 10: D1—SEM images of 15% PCL/5% EA/5% PEA with 10% Amox;
D2—SEM images of _15% PCL/5% EA/5% PEA with 20% Amox;
D3—SEM images of _15% PCL/5% EA/5% PEA with 40% Amox;
D1x—SEM images of _crosslinked_15% PCL/5% EA/5% PEA with 10% Amox;
D2x—SEM images of _crosslinked_15% PCL/5% EA/5% PEA with 20% Amox;
D3x—SEM images of crosslinked 15% PCL/5% EA/5% PEA with 40% Amox.

Where, $M_t$ is the amount of amoxicillin (amox) released at time t, $M_\infty$ is the amount of amox added to electrospinning solution. The release studies were done in duplicates & all samples were analyzed twice. FIG. 4 shows the release profile of NNF (neem based polyestermide nanofiber mat) for 10, 20 and 40% drug loaded nano-formulations. From the studies it was observed that there was no initial burst but for up to 10 h the release was faster and later it was slow and steady for up to 80 h. Release was more as the concentration of the drug increased in the nanofiber mats. 10% drug loaded nanofibers showed initial 30% release in 12 h followed by 50% release during 80 h. 20% and 40% drug loaded nanofibers showed 80-85% drug release during 80 h (FIG. 4).

Example 4

Antibacterial Study

The antimicrobial activity of the nanofibers containing amoxicillin was tested against *Staphylococcus aureus* as the model gram-positive bacteria. *Staphylococcus aureus* is the main bacteria which are responsible for the wound infection. The crosslinked electrospun nanofibers mats of with and without drug loaded were cut into disc shape with 1.0 cm diameter. Nanofiber mats without drug mats were used as control. The tests of antibacterial activities against *Staphylococcus aureus* (*S. aureus*, ATCC 25923) was carried out by Disc diffusion method. The disc diffusion method was performed in nutrient agar plate using a modified Kirby Bauer technique. The bacterial suspension (100 μl of $10^5$-$10^6$ colony forming units (CFU)) was dispersed uniformly on the surface of a nutrient agar plate before placing the test samples on it. Later the agar plates containing the test samples and control were incubated at 37° C. for 24 h and the inhibition zones surrounding the sample were measured. The bactericidal activity indicates a clear zone of inhibition within and around the nanofiber mat after an overnight incubation of the agar plate at 37° C.

The drug loaded nanofiber mat shows a clear zone of inhibition after 24 h that is observed and reported as in Table 3. It was observed that the drug loaded nanofiber mat shows clear zone of inhibition based on the drug activity against the susceptible bacteria (FIG. 3). By origin, the neem oil is antibacterial because of that its nanofiber mat shows more zone of inhibition rather than linseed based nanofibers and castor based nanofiber. The minimum inhibitory concentration of Amoxicillin was observed 0.05 to 8 µg/ml.

TABLE 3

Diameter of zone of inhibition of *S. aureus* growth on nutrient agar -

| Sr. No. | Formulation code | Zone of inhibition (mm) |
|---|---|---|
| 1. | NNF | 29 |
| 2. | LNF | 18 |
| 3. | CNF | 18 |

Example 5: Synthesis of HELA

To 3 eq. of diethanolamine in three necked RB, 1 eq. linseed oil was added and refluxed at 115° C. under nitrogen atm. After 6 h, the progress of reaction was monitored by TLC using 30% ethyl acetate in Pet ether.

Workup: To the reaction mixture added diethyl ether and washed with 15% NaCl solution then the organic layer dried with anhydrous sodium sulphate, concentrated by rotatory evaporator.

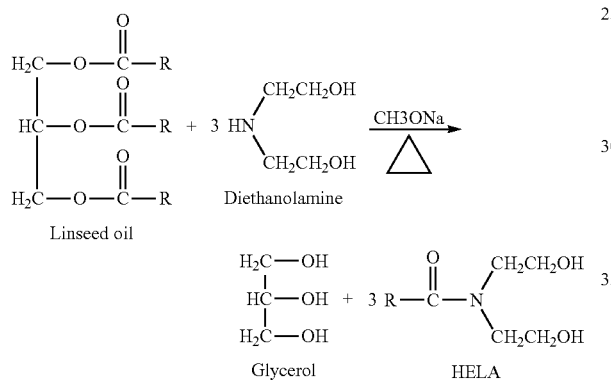

Example 6: Synthesis of PEA 1 eq. of HELA was taken in three necked round bottom (Rb) flask and dissolved in xylene then 1.5 eq. of Phthalic anhydride was added and it was refluxed at 145° C. under nitrogen atm. After 6 h, the progress of reaction was monitored with TLC using 30% ethyl acetate in Pet ether.

Workup: The reaction mixture diluted with xylene and then filtered with Whatman filter paper and then concentrated by rotatory evaporator.

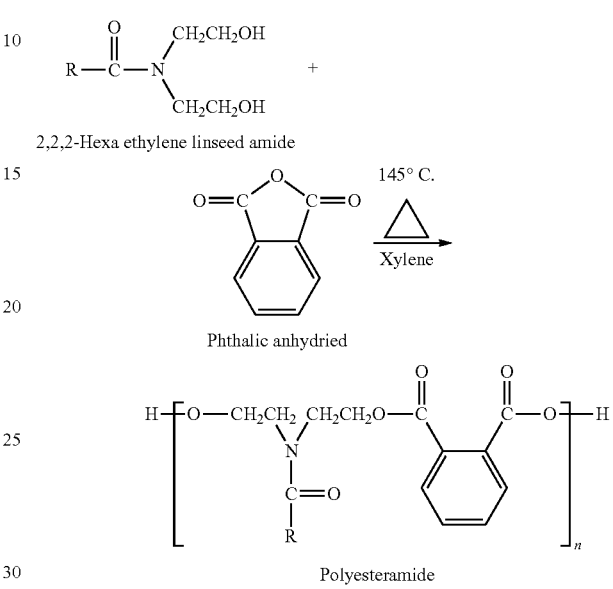

Example 7: Synthesis of Zn-PEA from HELA

HELA (1 eq) (5 gm) was taken in 3 necked Rb, equipped with dean stark apparatus and nitrogen gas inlet. Phthalic anhydride (2.65 gm) (1.2 eq.) and Zinc acetate (1.2 eq) (1.365 gm) was added and then the reaction mixture was heated up to 115° C. The progress of the reaction was monitored by TLC using 30% ethyl acetate in pet ether. Then the compound was dissolved in xylene and filtered to remove unreacted compounds. Finally solvent was evaporated on Rota evaporator.

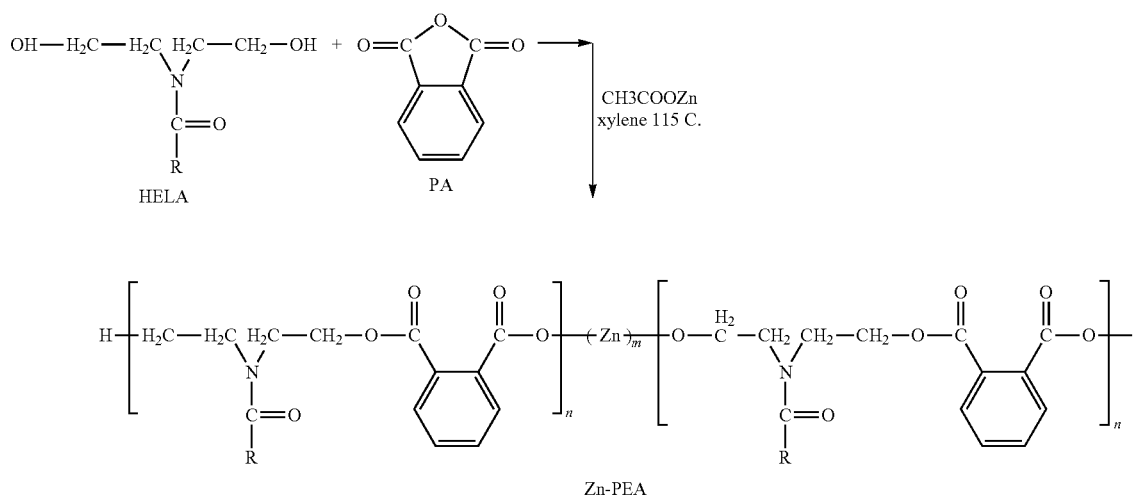

Example 8: Synthesis of Fe-PEA from HELA

HELA (1 eq) (5 gm) was taken in 3 necked Rb, equipped with dean stark apparatus with nitrogen gas inlet. Phthalic anhydride (2.65 gm) (1.2 eq.) and Fe(OH)$_2$ (1.2 eq) (1.365 gm) was added and then the reaction mixture was heated up to 70° C. The progress of the reaction was monitored by TLC using 30% ethyl acetate in pet ether. Then the compound was dissolved in xylene and filtered to remove un-reacted compounds. Finally solvent was evaporated on rota evaporator.

Example 10: Determination of $\lambda_{max}$ of Drug

A drug, chlorhexidine digluconate (20% in water) was purchased from Sigma Aldrich and it was diluted to 100 µg/ml. The $\lambda_{max}$ was determined using UV-Visible spectroscopy (Shimadzu UV-1601 PC UV visible double beam spectrometer), which was determined to be 255 nm. A standard curve was determined using various concentrations as shown in FIG. 16.

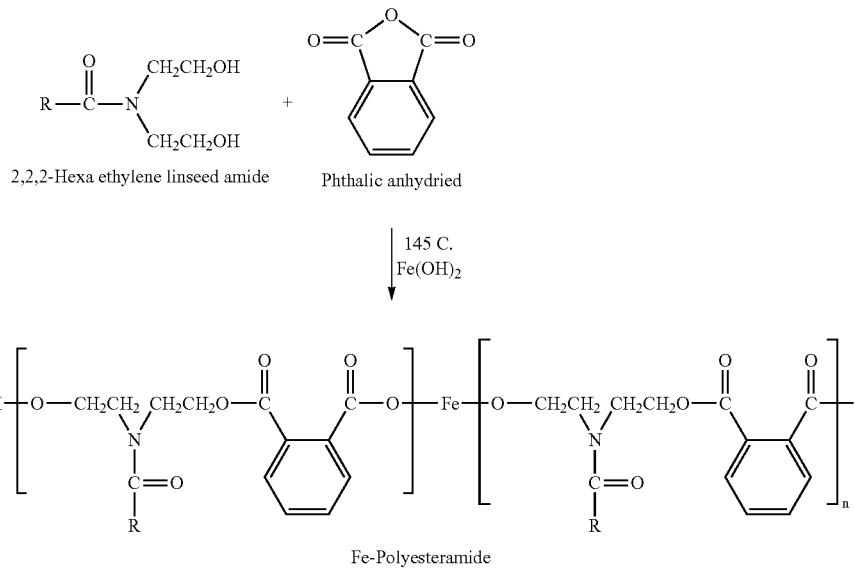

Example 9: Preparation of Blend of PHBV/EA/PEA for Electrospinning

PHBV, EA, Fe-PEA solution blends were prepared in different compositions as given in a Table 4, and were electrospun for obtaining nanofibers. Good nanofibers were obtained for 4% and 5% of the PHBV. Above 5%, PHBV was insoluble. PHBV, EA, Fe-PEA dissolved in HFIP and was Electrospurn at 15 KV, at a flow rate of 0.750 ml/h. The collector was kept at 10 cm from the tip of the syringe needle.

Example 11: Electrospinning with Different Concentrations of Drug (Chlorhexidine Digluconate)

One composition for nanofiber mats was selected and was electrospun with variable concentration of drug as given in Table 5 below and SEM images were taken for morphological observations and are described in FIGS. 11 and 12.

TABLE 4

Composition of Solution blends used for Electrospinning

| PHBV (%) | EA (%) | Fe-PEA (%) | Composition code | Total polymer concentration (%) | Solubility | Observation |
|---|---|---|---|---|---|---|
| 1 | 2 | 7 | S-1 | 10 | Soluble | No Nanofibers formed |
| 2 | 2 | 6 | S-2 | 10 | Soluble | No Nanofibers formed |
| 3 | 2 | 5 | S-3 | 10 | Soluble | No Nanofibers formed |
| 4 | 2 | 4 | S-4 | 10 | Soluble | Nanofibers were obtained |
| 5 | 2 | 3 | S-5 | 10 | Soluble | Nanofibers were obtained |
| 6 | 2 | 2 | S-6 | 10 | Insoluble | — |

TABLE 5

Composition for solution blend with addition of drug used for electrospinning

| Sr. No. | PHBV (%) | EA (%) | PEA (%) | Drug (%) | Composition code | Observations |
|---|---|---|---|---|---|---|
| 1 | 5 | 2 | 3 | 10 | S-7 | Nanofibers |
| 2 | 5 | 2 | 3 | 15 | S-8 | Nanofibers |
| 3 | 5 | 2 | 3 | 20 | S-9 | Nanofibers |

Example 12: Crosslinking of Nanofibers

Crosslinking of nanofibers was done by heating the nanofiber mats at 55-60° C. for 2 h. EA has sulfhydryl groups which on heating forms disulphide bonds (Rathna Gundloori 2011). During heating it is assumed that the adjacent polymeric chains overlapping nanofibers will be crosslinked holding the uncrosslinked PHBV polymer by entrapment. The ESEM images show the crosslinking of nanofiber mats as they stuck to each other (FIG. 12).

Example 13: Antimicrobial Study

The antimicrobial activity of synthesized PEA, Zn-PEA, Fe-PEA and drug (chlorhexidin digluconate) was tested against staphylococcus aureus which is a gram-positive bacteria and Escherichia-coli which is gram-negative bacteria. S. aureus is the most common bacterial species which is responsible for the wound infection and E-coli is commonly found in soil, water etc. henceforth that also could be responsible for wound infection. The antibacterial activity of newly synthesized polymers from linseed oil i.e., PEA, Zn-PEA and Fe-PEA were done against gram positive (S. aureus) and Gram negative (E-coli) was done. A loop full of suspension was inoculated in nutrient broth (peptone 5 gm/l, PH 6.8) and was incubated at room temperature for 28-30 hrs in a test tube shaker at 250 rpm. The actively growing bacterial cells were used for inhibition studies. The nutrient agar (20 ml, Autoclaved) was poured in petri dishes and allowed to solidify at a room temperature. After solidification 0.1 ml of bacterial culture was spread on nutrient agar and circular well was made using sterile steel boarer. All three PEA samples were prepared in Xylene as there is no effect of Xylene on a growth the test sample with different percentage were used for this study. This test samples were added to the wells and kept for incubation in incubator at room temperature for 24 hrs. After incubation zone of inhibition was measured in millimeter and represented as inactive (−), mild (+), moderate (++) and highly active (+++) (21) depending upon the diameter and clarity of zone.

Nanofibers mats without drug and with different concentration of drug incorporated into it was also used for antimicrobial study with the same microorganisms. The nanofibers with and without drug were cut into disk shaped 1.0 cm diameter structure and antimicrobial activities was tested by keeping nanofibers without drug as a control for this study by disk diffusion method. The disk diffusion method was performed in nutrient agar plate and bacterial culture was brought from national collection of industrial microorganisms (NCIM).

Figure 14:
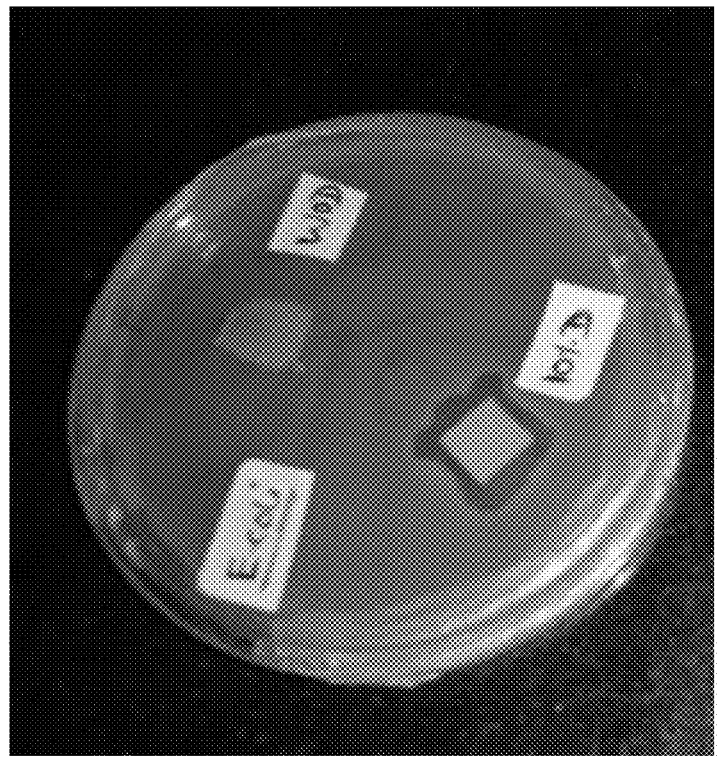
FIG. 14: Antibacterial studies of nano-fibers without drug and 10% drug using E. coli
Figure 15:
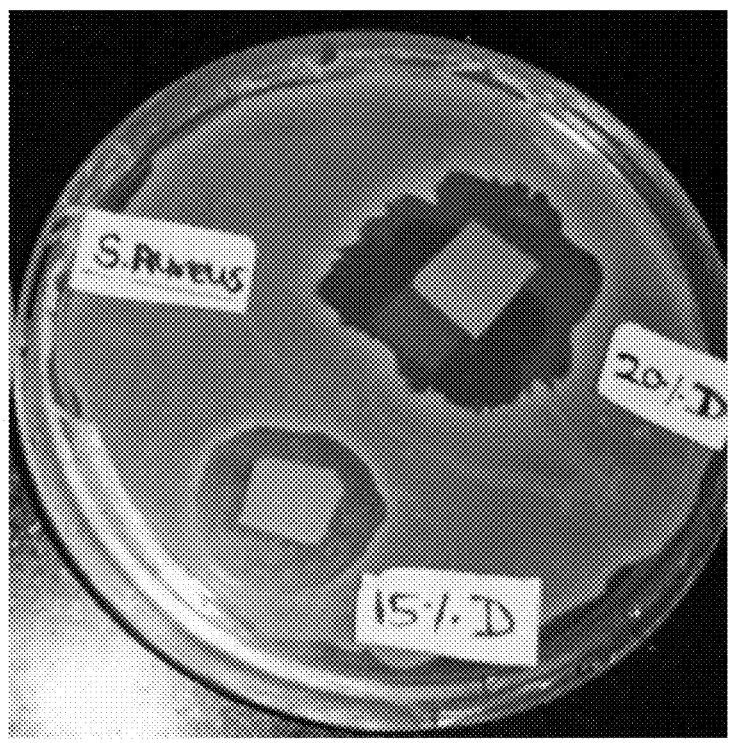
FIG. 15: Antibacterial studies of nanofibers loaded with 15% and 20% drug using S. aureus.

The bacterial suspension (100 μl of $10^5$-$10^6$) colony forming units (CFU) was dispersed uniformly on the surface of nutrient agar plate before placing the test sample on it. Then the agar plate containing the test sample with control were incubated at 37° C. for 24 hrs and the inhibition zones surrounding the samples were measured the bactericidal activity indicates the clear zones of inhibition within and around the compound, drug and nanofiber mats after an overnight incubation of the agar plate at 37° C. The growth inhibition zone of S. aureus and E-coli was measured and reported. The antibacterial activity is shown in FIGS. 13 to 15.

The invention claimed is:

1. A biocompatible and biodegradable nanofiber composition for wound healing and biomedical applications thereof, the biocompatible and biodegradable nanofiber composition comprising:
   0.1 to 20% hydrophobic polymer selected from the group consisting of polycaprolactone (PCL), polylactide, polyhydroxyalkonates, polyglycolide, 2-hydroxy ethyl cellulose, and poly(3-hydroxy butyric acid co-3-valeric acid) (PHBV);
   proteins that form disulfide crosslinks upon heating comprising egg albumin, bovine serum albumin (BSA) or human serum albumin;
   a polyesteramide of linseed, castor, or neem oil optionally incorporated with a transition metal ion; and
   a pharmaceutical drug,
   wherein the nanofiber composition is a crosslinked biodegradable mat, film, or gel.

2. The biocompatible and biodegradable nanofiber composition as claimed in claim 1, wherein the proteins that form disulfide crosslinks upon heating are present in an amount of from 0.1 to 15%.

3. The biocompatible and biodegradable nanofiber composition as claimed in claim 1, wherein the polyesteramide of linseed, castor, or neem oil is present in an amount of from 0.1 to 20%.

4. The biocompatible and biodegradable nanofiber composition as claimed in claim 1, wherein the pharmaceutical drug is in an amount of 5-22% w/w of the polymer.

5. The biocompatible and biodegradable nanofiber composition as claimed in claim 1, wherein a thickness of nanofibers formed from the biocompatible and biodegradable nanofiber composition is in the range of from 0.1 μm to 1 cm.

6. The biocompatible and biodegradable nanofiber composition as claimed in claim 1, wherein the pharmaceutical drug is selected from the group consisting of antibacterial agents, antimicrobial agents, antifungal agents, and antibiotics comprising amoxicillin, chlorhexidin digluconate, Cloxacillin, Dicloxacillin, Methicillin, Cephalosporin, Penicillin G, Penicillin V, neomycin, Neosporin, Mupiricin, Gentamicin, Clotrimazole, Mafenide acetate/nystatin, triclosan.

7. A process for preparation of a biocompatible and biodegradable nanofiber composition for wound healing and biomedical applications thereof, the process comprising the steps of:
   preparing a blend of 0.1 to 20% hydrophobic moiety polymer; proteins that form disulfide crosslinks upon heating comprising egg albumin, bovine serum albumin (BSA) or human serum albumin; polyesteramide of linseed, neem, or castor oil optionally incorporated with a transition metal ion; and a pharmaceutical drug;
   electrospinning the blend to obtain nanofibers; and
   crosslinking the nanofibers obtained by annealing at a temperature in a range of 50-100° C. to obtain a crosslinked biodegradable nanofiber mat, film, or gel.

8. A method of treating a subject with burns, acne, lesions, injuries, cuts, or wounds, the method comprising applying to an affected area a biocompatible and biodegradable nanofiber composition comprising:

0.1 to 20% of a hydrophobic polymer selected from the group consisting of polycaprolactone, polylactide, polyhydroxyalkonates, polyglycolide, and poly(3-hydroxy butyric acid co-3-valeric acid);

proteins that form disulfide bonds upon beating comprising egg albumin, bovine serum albumin (BSA), or human serum albumin;

a polyesteramide of linseed, castor, or neem oil optionally incorporated with a transition metal ion; and a pharmaceutical drug, wherein the nanofiber composition is a crosslinked biodegradable mat, film, or gel less.

* * * * *

UNITED STATES PATENT AND TRADEMARK OFFICE
CERTIFICATE OF CORRECTION

PATENT NO. : 10,195,158 B2  
APPLICATION NO. : 15/116021  
DATED : February 5, 2019  
INVENTOR(S) : Gundloori Page 1 of 2

It is certified that error appears in the above-identified patent and that said Letters Patent is hereby corrected as shown below:

In the Drawings

Figure 5:
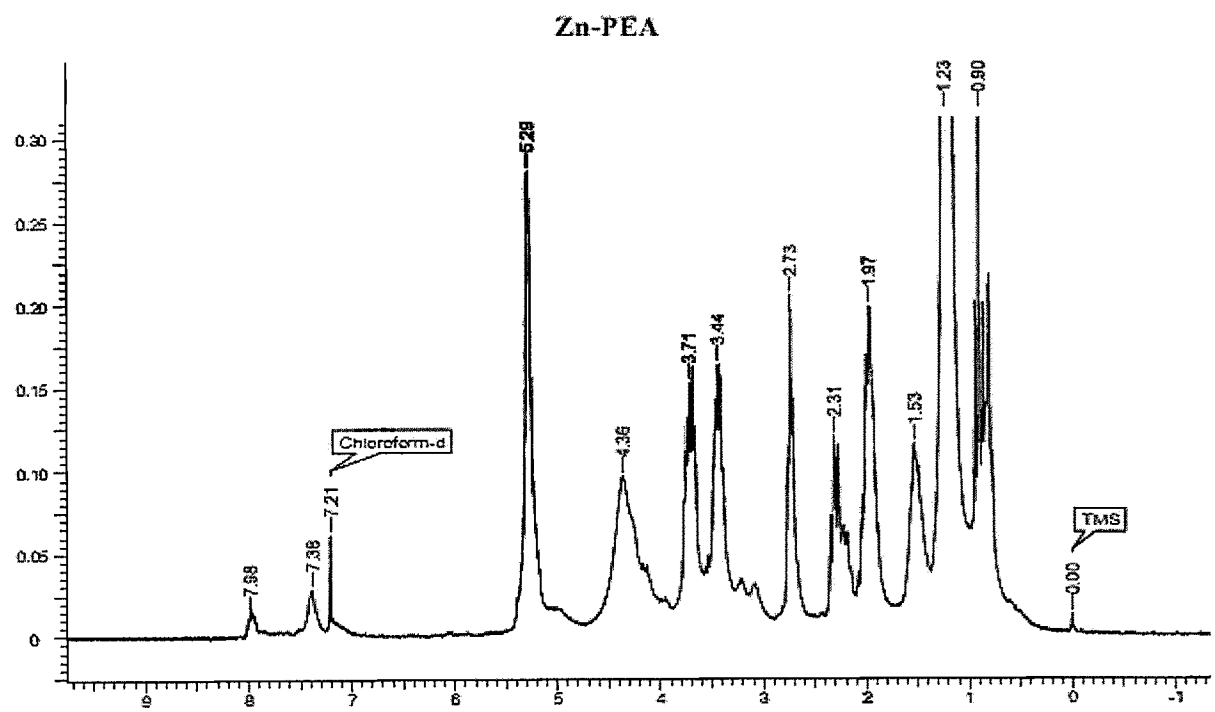
FIG. 5: NMR of Zn-PEA.

Delete fig. 5, and substitute therefor the drawing sheet, consisting of fig. 5, as shown on the attached page.

In the Claims

Column 18,
Line 50, "Methicillin, Cephalosporin" should read --Methicillin, Oxacillin, Cephalosporin--.

Column 19,
Line 9, "proteins that form disulfide bonds upon beating" should read --proteins that form disulfide bonds upon heating--;
Line 16, "degradable mat, film, or gel less." should read --degradable mat, file, or gel.--.

Signed and Sealed this
Third Day of September, 2019

Andrei Iancu
*Director of the United States Patent and Trademark Office*